United States Patent
Yang et al.

(10) Patent No.: US 11,117,967 B2
(45) Date of Patent: Sep. 14, 2021

(54) ANTIBODY SPECIFICALLY BINDING TO PD-1 AND FUNCTIONAL FRAGMENT THEREOF

(71) Applicant: Beijing Hanmi Pharm. Co., LTD., Beijing (CN)

(72) Inventors: Yaping Yang, Beijing (CN); Jiawang Liu, Beijing (CN); Nanmeng Song, Beijing (CN); Hongjuan Zhang, Beijing (CN); Mengxie Jin, Beijing (CN)

(73) Assignee: BEIJING HANMI PHARM. CO., LTD., Beijing (CN)

( * ) Notice: Subject to any disclaimer, the term of this patent is extended or adjusted under 35 U.S.C. 154(b) by 256 days.

(21) Appl. No.: 16/332,880

(22) PCT Filed: Sep. 8, 2017

(86) PCT No.: PCT/CN2017/101082
§ 371 (c)(1),
(2) Date: Mar. 13, 2019

(87) PCT Pub. No.: WO2018/050027
PCT Pub. Date: Mar. 22, 2018

(65) Prior Publication Data
US 2019/0367615 A1 Dec. 5, 2019

(30) Foreign Application Priority Data
Sep. 14, 2016 (CN) .......................... 201610827099.1

(51) Int. Cl.
| | | |
|---|---|---|
| A61K 39/00 | (2006.01) |
| C07K 16/28 | (2006.01) |
| A61K 47/68 | (2017.01) |
| A61P 35/00 | (2006.01) |
| A61K 49/00 | (2006.01) |
| A61K 49/16 | (2006.01) |
| A61K 49/22 | (2006.01) |
| A61K 51/10 | (2006.01) |

(52) U.S. Cl.
CPC ...... *C07K 16/2818* (2013.01); *A61K 47/6803* (2017.08); *A61K 47/6849* (2017.08); *A61K 49/0058* (2013.01); *A61K 49/16* (2013.01); *A61K 49/221* (2013.01); *A61K 51/1027* (2013.01); *A61P 35/00* (2018.01); *A61K 2039/505* (2013.01); *C07K 2317/24* (2013.01); *C07K 2317/76* (2013.01); *C07K 2317/92* (2013.01)

(58) Field of Classification Search
CPC .............................................. A61K 2039/505
See application file for complete search history.

(56) References Cited

U.S. PATENT DOCUMENTS

| 10,066,013 B2 | 9/2018 | Chen et al. |
|---|---|---|
| 2010/0266617 A1 | 10/2010 | Carven et al. |
| 2016/0376367 A1 | 12/2016 | Yuan et al. |
| 2017/0240644 A1 | 8/2017 | Zhou et al. |

FOREIGN PATENT DOCUMENTS

| CN | 104250302 A | 12/2014 |
|---|---|---|
| CN | 104479020 A | 4/2015 |
| CN | 104945508 A | 9/2015 |
| CN | 105061597 A | 11/2015 |
| CN | 105175544 A | 12/2015 |
| CN | 105566496 A | 5/2016 |
| EP | 3026062 A1 | 6/2016 |
| WO | 2008156712 A1 | 12/2003 |
| WO | 2011110621 A1 | 9/2011 |
| WO | 2015026684 A1 | 2/2015 |
| WO | 2015035606 A1 | 3/2015 |
| WO | 2015085847 A1 | 6/2015 |
| WO | 2015112900 A1 | 7/2015 |
| WO | 2016014688 A2 | 1/2016 |

OTHER PUBLICATIONS

International Search Report issued in PCT International Application No. PCT/CN2017/101082, dated Nov. 22, 2017, 16 pages.
Afreen et al., "The immunoinhibitory B7-H1 molecule as a potential target in cancer: Killing many birds with one stone," Hematol Oncol Stem Cell Ther 7(1), First Quarter 2014, 17 pages.
Gianchecchi et al., "Recent insights into the role of the PD1/PD-L1 pathway in immunological tolerance and autoimmunity," Autoimmunity Reviews 12 (2013) 1091-1100.
James et al., "Combination immune therapies to enhance anti-tumor responses by NK cells," Frontiers in Immunology, Dec. 2013, vol. 4, Article 481, 12 pages.
Kim et al., "Prospects for Targeting PD-1 and PD-L1 in Various Tumor Types," Oncology Journal, Supplements, Nov. 11, 2014, vol. 28, Issue: 11, Suppl. 3, 12 pages.
Motz et al., "Deciphering and Reversing Tumor Immune Suppression," Immunity 39, Jul. 25, 2013, 61-73.
Ohaegbulam et al., "Human cancer immunotherapy with antibodies to the PD-1 and PD-L1 pathway," Trends in Molecular Medicine, Jan. 2015, vol. 21, No. 1, 24-33.
Pardoll, "The blockade of immune checkpoints in cancer immunotherapy," Nature, Apr. 2012, vol. 12, 252-264.
Pilotto et al., "Immune Checkpoint Inhibitors for Non-small-cell Lung Cancer: Does that Represent a 'New Frontier'?," Anti-Cancer Agents in Medicinal Chemistry, 2015, vol. 15, 7 pages.
Postow et al., "Immune Checkpoint Blockade in Cancer Therapy," Journal of Clinical Oncology, vol. 33, No. 17, Jun. 10, 2015, 1974-1982.

(Continued)

Primary Examiner — Stephen L Rawlings
(74) Attorney, Agent, or Firm — RatnerPrestia

(57) ABSTRACT

An antibody specifically binding to PD-1 and a functional fragment thereof. The antibody or functional fragment thereof includes a PD-1 chimeric antibody and a functional fragment thereof, and a PD-1 humanized antibody and a functional fragment thereof.

37 Claims, 6 Drawing Sheets

Specification includes a Sequence Listing.

(56) References Cited

OTHER PUBLICATIONS

Canadian Office Action for Canadian Application No. 3,036,912, dated Jan. 6, 2020, 3 pages.
Extended European Search Report for European Application No. 17 850 229.0, dated Apr. 14, 2020, 10 pages.
Melero et al., "Clinical Development of Immunostimulatory Monoclonal Antibodies and Opportunities for Combination"; Clinical Cancer Research, 2013, vol. 19, pp. 997-1008.
Dominican Republic Office Action issued in Application No. P20190064, dated Jan. 12, 2021 with translation, 7 pages.

ANTIBODY SPECIFICALLY BINDING TO PD-1 AND FUNCTIONAL FRAGMENT THEREOF

CROSS REFERENCE TO RELATED APPLICATIONS

This application is the U.S. National Phase Application of PCT/CN2017/101,082, filed Sep. 8, 2017, which claims priority to Chinese Patent Application No. CN201610827099.1, filed on Sep. 14, 2016 with State Intellectual Property Office and entitled "Antibody Specifically Binding to PD-1 and Functional Fragment Thereof", the contents of such applications being incorporated herein by reference herein.

FIELD

The present disclosure relates to the field of medical biotechnology and humanized antibody engineering research, and in particular to an antibody specifically binding to PD-1 and functional fragments thereof.

BACKGROUND

Programmed death-1 (PD-1) is a recently-advanced immune checkpoint involved in the regulation of T cell activation, which can regulate the strength and duration of immune responses. Under normal conditions, PD-1 can mediate and maintain the autoimmune tolerance of the body and prevent the excessive activation of the immune system during the inflammatory reaction which causes damages to tissues, having a positive effect on avoiding the occurrence of autoimmune diseases. Under pathological conditions, PD-1 involves in tumor immunity as well as the occurrence and development of various autoimmune diseases (Anticancer Agents Med Chem. 2015; 15(3):307-13. Hematol Oncol Stem Cell Ther. 2014 March; 7(1):1-17. Trends Mol Med. 2015 January; 21(1):24-33. Immunity. 2013 Jul. 25; 39(1): 61-73. J Clin Oncol. 2015 Jun. 10; 33(17):1974-82).

PD-1 belongs to the CD28 family. But unlike other members of the CD28 family, such as CTLA4, which can form a covalent dimer linked by a disulfide bond, PD-1 exists as a monomer. The structure of PD-1 mainly includes the extracellular immunoglobulin variable region-like domain, the hydrophobic transmembrane region and the intracellular region, and the intracellular region has two independent phosphorylation sites, that is, the immunoreceptor tyrosine-based inhibitory motif and the immunoreceptor tyrosine-based switch motif, respectively. The expression of PD-1 is inducible, and mainly on the surface of activated T cells and also B cells, NK cells, monocytes, and DC cells. The ligand of PD-1 includes PD-L (programmed death ligand 1), PD-L2 (programmed death ligand 2), and its ligands belong to the B7 family. PD-L1 may be induced and expressed on various immune cell surfaces including T cells, B cells, monocytes, macrophages, DC cells, and endothelial cells, epidermal cells, etc., while PD-L2 may be induced and expressed on some immune cells including macrophages, DC cells, B cells (Autoimmun Rev, 2013, 12(11): 1091-1100; Front Immunol, 2013, 4: 481. Nat Rev Cancer, 2012, 12(4): 252-264; Trends Mol Med. 2015 January; 21(1):24-33).

It has been found in tumor studies that PD-L1 is highly expressed on cell surfaces of a variety of tumors, including melanoma, lung cancer, kidney cancer, breast cancer, ovarian cancer, cervical cancer, bladder cancer, esophageal cancer, gastric cancer, pancreatic cancer, and intestinal cancer, while PD-L2 is highly expressed on cell surfaces of B cell lymphoma. Through highly expressed PD-L1 or PD-L2, tumor cells bind to PD-1 on T cells, and transmit immunosuppressive signals, resulting in body immune tolerance to tumor cells, which is beneficial to the growth and metastasis of tumor cells. The high expression of PD-1 ligand is closely related to poor prognosis and drug resistance in tumor patients (Hematol Oncol Stem Cell Ther., 2014 March; 7(1):1-17). Moreover, studies have also found that up-regulated expression of PD-1 on the surface of T cells, especially on the surface of T cells infiltrated within tumor cells, is also closely related to poor prognosis (Trends Mol Med., 2015 January; 21(1):24-33).

It is a recent hot spot to develop antibodies that block the PD-1/PD-Ls signaling pathway to fight tumors. Clinically, PD-1/PD-Ls blocking antibodies have two distinct features: first, the efficacy is not limited to a certain tumor type, the strong and long-lasting anti-tumor efficacy is in a broad spectrum of tumors, as clinical evaluation involves more and more tumor types, this feature will be further verified. Second, the safety of these antibodies is pretty good, and only has some immune-related side effects, instead of those common side effects of some chemotherapeutic drugs and targeted drugs, such as fatigue, white blood cell reduction, baldness, diarrhea and rash. The PD-1 antibody Nivolumab has been marketed for the treatment of advanced melanoma, non-small cell lung cancer and renal cell carcinoma, and Pembrolizuamb has been marketed for the treatment of advanced melanoma and non-small cell lung cancer. A problem worthy to be pointed out is that current good anti-tumor efficacy of PD-1/PD-Ls blocking antibodies can only benefit a small number of patients, most patients have innate drug resistance, or will develop secondary drug resistance (Oncology (Williston Park), 2014 Nov.; 28 Suppl 3:15-28).

In view of this, the present disclosure has been specifically proposed.

SUMMARY

The present disclosure is based on an obtained parental anti-human PD-1 murine monoclonal antibody having the ability to specifically bind to human PD-1 protein, by cloning, identification and gene structure analysis to determine its CDR region, construct corresponding chimeric antibody and humanized antibody, establish corresponding eukaryotic cell expression system and produce and purify the chimeric antibody and the humanized antibody.

In order to achieve the above goal of the present disclosure, the following technical solutions are specially adopted:

An antibody capable of specifically binding to PD-1 and functional fragment thereof, wherein the antibody or the functional fragment comprises a light chain and a heavy chain;

the light chain comprises a light chain CDR consisting of CDR-L1, CDR-L2 and CDR-L3; the heavy chain comprises a heavy chain CDR consisting of CDR-H1, CDR-H2 and CDR-H3;

the amino acid sequences of the CDR-L1, CDR-L2, and CDR-L3 are respectively set forth in SEQ ID NO: 1, 5 and 6, or respectively set forth in SEQ ID NO: 2, 5 and 6, or respectively set forth in SEQ ID NO: 3, 5 and 6, or respectively set forth in SEQ ID NO: 4, 5 and 6; the amino acid sequences of the CDR-H1, CDR-H2, and CDR-H3 are respectively set forth in SEQ ID NO: 7, 8 and 9.

Preferably, the antibody or the functional fragment thereof includes a PD-1 chimeric antibody and a functional fragment thereof, and a PD-1 humanized antibody and a functional fragment thereof. That is, it may also be interpreted as that the antibody or the functional fragment thereof includes a PD-1 chimeric antibody and a functional fragment thereof, or the antibody or the functional fragment thereof includes a PD-1 humanized antibody and a functional fragment thereof.

It is well known in the art that both the binding specificity and affinity of an antibody are mainly determined by the CDR, and the amino acid sequence of the non-CDR region can be easily changed according to the well-known existing techniques to obtain a variant having similar biological activities. In the present disclosure, the monoclonal antibody variants have CDR sequences identical to the CDR sequences of above-mentioned humanized antibodies, thus, they have similar biological activities.

Preferably, the antibody and the functional fragment thereof as described above, wherein the antibody comprises a constant region sequence of any one selected from the group consisting of human IgG1, IgG2, IgG3, IgG4, IgA, IgM, IgE and IgD.

Preferably, antibody and the functional fragment thereof as described above, wherein the functional fragment comprises one or more selected from the group consisting of $F(ab')_2$, Fab', Fab, Fv, scFv, bispecific antibody and antibody minimal recognition unit.

The "functional fragment" of the present disclosure specifically refers to an antibody fragment having the same specificity to PD-1 as that of the parent antibody. In addition to the above mentioned functional fragments, any fragment of which half-life has been increased may be also included.

scFv (sc=single strand), bispecific antibody (diabodies).

These functional fragments typically have the same binding specificity as the antibody from which they are derived. One ordinary skill in the art can learn from what is described in the specification of the present disclosure that the antibody fragment of the present disclosure and obtain the above mentioned function fragment by a method such as enzymatic digestion (including pepsin or papain) and/or a method of chemically reducing split disulfide bonds.

The antibody fragments can also be obtained by peptide synthesis by recombinant genetic techniques, which are also known to those having ordinary skill in the art, or by automated peptide synthesizers such as an automated peptide synthesizer sold by such as Applied BioSystems.

Preferably, the antibody and the functional fragment thereof as described above, wherein the amino acid sequences of light chain variable region and heavy chain variable region of the PD-1 chimeric antibody and the functional fragment thereof are respectively set forth in SEQ ID NO: 10 and SEQ ID NO: 14, or respectively set forth in SEQ ID NO: 11 and SEQ ID NO:14, or respectively set forth in SEQ ID NO: 12 and SEQ ID NO: 14, or respectively set forth in SEQ ID NO: 13 and SEQ ID NO: 14.

Further preferably, the antibody and the functional fragment thereof as described above, wherein the amino acid sequences of the light chain constant region and the heavy chain constant region of the PD-1 chimeric antibody and the functional fragment thereof are respectively set forth in SEQ ID NO: 15 and SEQ ID NO: 16.

Preferably, the antibody and the functional fragment thereof as described above, wherein light chain framework region of the PD-1 humanized antibody and the functional fragment thereof comprises FR-L1, FR-L2, FR-L3 and FR-L4, and heavy chain framework region of the PD-1 humanized antibody and the functional fragment thereof comprises FR-H1, FR-H2, FR-H3 and FR-H4;

the FR-L1 is selected from the amino acid sequence set forth in SEQ ID NO: 17 and the amino acid sequence having the following substitution or a combination thereof:
the $1^{st}$ amino acid D is replaced by E;
the $2^{nd}$ amino acid V is replaced by I;
the $13^{th}$ amino acid L is replaced by V;
the $19^{th}$ amino acid A is replaced by V;
the FR-L2 is selected from the amino acid sequence set forth in SEQ ID NO: 18 and the amino acid sequence having the following substitution or a combination thereof:
the $6^{th}$ amino acid P is replaced by S;
the $7^{th}$ amino acid G is replaced by H;
the $9^{th}$ amino acid A is replaced by S;
the FR-L3 is selected from the amino acid sequence set forth in SEQ ID NO: 19 and the amino acid sequence having the following substitution or a combination thereof:
the $22^{th}$ amino acid L is replaced by V;
the $24^{th}$ amino acid P is replaced by T;
the $28^{th}$ amino acid A is replaced by G;
the $31^{th}$ amino acid F is replaced by Y;
the FR-L4 is selected from the amino acid sequence set forth in SEQ ID NO: 20 and the amino acid sequence having the following substitution or a combination thereof:
the $7^{th}$ amino acid V is replaced by L;
the FR-H1 is selected from the amino acid sequence set forth in SEQ ID NO: 21;
the FR-H2 is selected from the amino acid sequence set forth in SEQ ID NO: 22 and the amino acid sequence having the following substitution or a combination thereof:
the $5^{th}$ amino acid A is replaced by T;
the $14^{th}$ amino acid A is replaced by S;
the FR-H3 is selected from the amino acid sequence set forth in SEQ ID NO: 23 and the amino acid sequence having the following substitution or a combination thereof:
the $12^{th}$ amino acid N is replaced by T;
the $14^{th}$ amino acid Y is replaced by H;
the $18^{th}$ amino acid N is replaced by S;
the FR-H4 is selected from the amino acid sequence set forth in SEQ ID NO: 24.

Usually, when transplanting CDRs of a murine antibody to a human framework, selection of a human framework with high sequence homology will have a certain success rate. However, studies have shown that many CDR grafts require a back mutation to restore certain antibody activity. How to choose the right human source framework is the major bottleneck.

The CDR is the major relevant site for antigen binding, but in most cases, the FR (framework region) has a significant influence on the conformation of the binding site. In order to obtain a high affinity humanized antibody, in the present disclosure, a suitable FR region is selected and the relevant FR residue is reversed back to the original murine amino acid or a amino acid presented in human and having the same function.

Preferably, light chain variable region sequence of the PD-1 humanized antibody and the functional fragment thereof is one selected from SEQ ID NO: 25 to 36;
preferably, heavy chain variable region sequence of the PD-1 humanized antibody and the functional fragment thereof is one selected from SEQ ID NO: 37 to 42;
more preferably, the light chain variable region sequence of the PD-1 humanized antibody and the functional fragment thereof is set forth in SEQ ID NO: 25; the corresponding heavy chain variable region sequence is set forth in SEQ ID NO: 37;

alternatively, the light chain variable region sequence of the PD-1 humanized antibody and functional fragment thereof is set forth in SEQ ID NO: 25; the corresponding heavy chain variable region sequence is set forth in SEQ ID NO: 38;

alternatively, the light chain variable region sequence of the PD-1 humanized antibody and functional fragment thereof is set forth in SEQ ID NO: 29; the corresponding heavy chain variable region sequence is set forth in SEQ ID NO: 38;

alternatively, the light chain variable region sequence of the PD-1 humanized antibody and functional fragment thereof is set forth in SEQ ID NO: 30; the corresponding heavy chain variable region sequence is set forth in SEQ ID NO: 38;

alternatively, the light chain variable region sequence of the PD-1 humanized antibody and functional fragment thereof is set forth in SEQ ID NO: 31; the corresponding heavy chain variable region sequence is set forth in SEQ ID NO: 38;

alternatively, the light chain variable region sequence of the PD-1 humanized antibody and functional fragment thereof is set forth in SEQ ID NO: 26; the corresponding heavy chain variable region sequence is set forth in SEQ ID NO: 38;

alternatively, the light chain variable region sequence of the PD-1 humanized antibody and functional fragment thereof is set forth in SEQ ID NO: 28; the corresponding heavy chain variable region sequence is set forth in SEQ ID NO: 40;

alternatively, the light chain variable region sequence of the PD-1 humanized antibody and functional fragment thereof is set forth in SEQ ID NO: 25; the corresponding heavy chain variable region sequence is set forth in SEQ ID NO: 40;

alternatively, the light chain variable region sequence of the PD-1 humanized antibody and functional fragment thereof is set forth in SEQ ID NO: 29; the corresponding heavy chain variable region sequence is set forth in SEQ ID NO: 40;

alternatively, the light chain variable region sequence of the PD-1 humanized antibody and functional fragment thereof is set forth in SEQ ID NO: 30; the corresponding heavy chain variable region sequence is set forth in SEQ ID NO: 40;

alternatively, the light chain variable region sequence of the PD-1 humanized antibody and functional fragment thereof is set forth in SEQ ID NO: 31; the corresponding heavy chain variable region sequence is set forth in SEQ ID NO: 40;

alternatively, the light chain variable region sequence of the PD-1 humanized antibody and functional fragment thereof is set forth in SEQ ID NO: 28; the corresponding heavy chain variable region sequence is set forth in SEQ ID NO: 38;

alternatively, the light chain variable region sequence of the PD-1 humanized antibody and functional fragment thereof is set forth in SEQ ID NO: 27; the corresponding heavy chain variable region sequence is set forth in SEQ ID NO: 39;

alternatively, the light chain variable region sequence of the PD-1 humanized antibody and functional fragment thereof is set forth in SEQ ID NO: 32; the corresponding heavy chain variable region sequence is set forth in SEQ ID NO: 39;

alternatively, the light chain variable region sequence of the PD-1 humanized antibody and functional fragment thereof is set forth in SEQ ID NO: 33; the corresponding heavy chain variable region sequence is set forth in SEQ ID NO: 39;

alternatively, the light chain variable region sequence of the PD-1 humanized antibody and functional fragment thereof is set forth in SEQ ID NO: 34; the corresponding heavy chain variable region sequence is set forth in SEQ ID NO: 39;

alternatively, the light chain variable region sequence of the PD-1 humanized antibody and functional fragment thereof is set forth in SEQ ID NO: 35; the corresponding heavy chain variable region sequence is set forth in SEQ ID NO: 41;

alternatively, the light chain variable region sequence of the PD-1 humanized antibody and functional fragment thereof is set forth in SEQ ID NO: 36; the corresponding heavy chain variable region sequence is set forth in SEQ ID NO: 42;

more preferably, the amino acid sequences of the light chain constant region sequence and the heavy chain constant region sequence of the PD-1 humanized antibody and the functional fragment thereof are set forth in SEQ ID NO: 15 and SEQ ID NO: 16, respectively.

It should be noted that, in addition to the above-mentioned amino acid sequences in the present application, the production of chimeric antibodies and humanized antibodies can be achieved by any method known by those having ordinary skill in the art, such as by designing recombinant humanized antibody based on sequenced CDRs of murine antibodies, the murine antibody is secreted by myeloma cells from immunized mice or by myeloma cells fused to splenocytes of other species which fused to myeloma cells. The immunized animal may include a transgenic mouse having a human immunoglobulin locus which can directly produce a human antibody. Another possible embodiment may include screening the library using phage display technology.

An isolated nucleic acid molecule, which is selected from:
A) DNA or RNA encoding the antibody and the functional fragment thereof as described above; and
B) a nucleic acid complementary to the nucleic acid defined in A).

A vector, which contains a nucleic acid molecule as described above.

The present disclosure further provides at least one nuclear construct encoding a nucleic acid molecule as described above, preferably a vector, more preferably an expression vector, such as a plasmid, which is described in one embodiment of the present application.

A host cell, which is transformed with a vector as described above.

The host cell is a eukaryotic cell, such as a mammalian cell.

A method of producing an antibody capable of specifically binding to PD-1 and a functional fragment thereof includes the following steps:
culturing host cells as described above in a medium and under suitable culture conditions; and
recovering produced antibody and its functional fragments from the culture medium or from the cultured host cells.

A composition, which comprises the antibody and/or the functional fragment thereof, or a compound of the antibody and other components, or a compound of the antibody functional fragment and other components, as an active ingredient.

Preferably, the composition as described above, the antibody and the functional fragment thereof are coupled to at least one diagnostic agent and/or therapeutic agent to form an immunoconjugate.

Preferably, the diagnostic agent is one or more selected from the group consisting of a radionuclide, a radioactive contrast agent, a paramagnetic ion, a metal, a fluorescent label, a chemiluminescent label, an ultrasound contrast agent, and a photosensitizer.

Preferably, the radionuclide is one or more selected from the group consisting of $^{110}$In, $^{111}$In, $^{177}$Lu, $^{18}$F, $^{52}$Fe, $^{62}$Cu, $^{64}$Cu, $^{67}$C, $^{67}$Ga, $^{68}$Ga, $^{86}$Y, $^{90}$Y, $^{89}$Zr, $^{94}$mTc, $^{94}$Tc, $^{99}$mTc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52}$mMn, $^{55}$Co, $^{72}$As, $^{75}$Br, $^{76}$Br, $^{82}$mRb and $^{83}$Sr.

Preferably, the paramagnetic ion is one or more selected from the group consisting of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III).

Preferably, the fluorescent label is one or more selected from the group consisting of Alexa 350, Alexa 405, Alexa 430, Alexa 488, Alexa 555, Alexa 647, AMCA, aminoacridine, BODIPY 630/650, BODIPY 650/665, BODIPY-FL, BODIPY-R6G, BODIPY-TMR, BODIPY-TRX, 5-carboxy-4', 5'-dichloro-2', 7'-dimethoxyfluorescence, 5-carboxy-2',4', 5',7'-tetrachlorofluorescein, 5-carboxyfluorescein, 5-carboxyrhodamine, 6-carboxyrhodamine, 6-carboxytetramethylrhodamine, Cascade Blue, Cy2, Cy3, Cy5, Cy7, 6-FAM, dansyl chloride, fluorescein, H-EX, 6-JOE, NBD (7-nitrobenzo-2-oxa-1,3-diazole), Oregon Green 488, Oregon Green 500, Oregon Green 514, Pacific Blue, phthalic acid, terephthalic acid, isophthalic acid, cresol fast violet, cresyl violet, brilliant cresyl blue, 4-Aminobenzoic acid, erythrosine, phthalocyanine, azomethine, cyanine, xanthine, succinyl fluorescein, rare earth metal cryptate, tri-bipyridyldiamine oxime, europium cryptate compound or chelate, diamine, dicyanine, La Jolla blue dye, allophycocyanin, allococyanin B, phycocyanin C, phycocyanin R, thiamine, R-phycoerythrin, C-Phycocyanin, phycoerythrin R, REG, rhodamine green, rhodamine isothiocyanate, rhodamine red, ROX, TAMRA, TET, TRIT (tetramethylrhodamine isothiol), tetramethylrhodamine and Texas Red.

Preferably, the therapeutic agent is one or more selected from the group consisting of a naked antibody, a cytotoxic agent, a drug, a radionuclide, a boron atom, an immunomodulator, an anti-apoptotic agent, a photosensitizing therapeutic, an immunoconjugates and a oligonucleotide.

Preferably, the drug is one or more selected from the group consisting of methotrexate, fluorouracil, mercaptopurine, hydroxyurea, cytarabine, nitrogen mustard, cyclophosphamide, thiotepa, cisplatin, mitomycin, bleomycin, camptothecin, podophyllotoxin, actinomycin D, doxorubicin, daunorubicin, vinblastine, paclitaxel, cephalotaxus alkaloids and L-asparaginase.

Preferably, the oligonucleotide is one or more selected from the group consisting of shRNA, miRNA and siRNA.

Preferably, the immunomodulator is one or more selected from the group consisting of a cytokine, a chemokine, a stem cell growth factor, a lymphotoxin, a hematopoietic factor, a colony stimulating factor (CSF), an interferon, an erythropoietin, a thrombopoietin, a tumor necrosis factor (TNF), an interleukin (IL), granulocyte-colony stimulating factor (G-CSF), granulocyte macrophage-colony stimulating factor (GM-CSF) and stem cell growth factor.

Wherein, the cytokine is preferably one or more selected from the group consisting of human growth hormone, N-methionyl human growth hormone, bovine growth hormone, parathyroid hormone, thyroxine, insulin, proinsulin, relaxin, prorelaxin, follicle-stimulating hormone (FSH), thyroid stimulating hormone (TSH), luteinizing hormone (LH), liver growth factor, prostaglandin, fibroblast growth factor, prolactin, placental lactogen, OB protein, tumor necrosis factor-α, tumor necrosis factor-β, Mullerian inhibitor, mouse gonadotropin-related peptide, inhibin, activin, vascular endothelial growth factor, integrin, thrombopoietin (TPO), NGF-β, platelet-growth factor, TGF-α, TGF-β, insulin-like growth factor-I, insulin-like growth factor-II, erythropoietin (EPO), osteoinductive factor, interferon-α, interferon-β, interferon-γ, macrophage-CSF (M-CSF), IL-1, IL-1a, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, IL-25, LIF, FLT-3, angiostatin, thrombospondin, endostatin, tumor necrosis factor and LT.

The chemokine is preferably one or more selected from the group consisting of RANTES, MCAF, MIP1-α, MIP1-β, and IP-10.

Preferably, the radionuclide is one or more selected from the group consisting of $^{111}$In, $^{111}$At, $^{177}$Lu, $^{211}$Bi, $^{212}$Bi, $^{213}$Bi, $^{211}$At, $^{62}$Cu, $^{67}$Cu, $^{90}$Y, $^{125}$I, $^{131}$I, $^{133}$I, $^{32}$P, $^{33}$P, $^{47}$Sc, $^{111}$Ag, $^{67}$Ga, $^{153}$Sm, $^{161}$Tb, $^{152}$Dy, $^{166}$Dy, $^{161}$Ho, $^{166}$Ho, $^{186}$Re, $^{188}$Re, $^{189}$Re, $^{211}$Pb, $^{212}$Pb, $^{223}$Ra, $^{225}$Ac, $^{77}$As, $^{89}$Sr, $^{99}$Mo, $^{105}$Rh, $^{149}$Pm, $^{169}$Er, $^{194}$Ir, $^{58}$Co, $^{80}$mBr, $^{99}$mTc, $^{103}$mRh, $^{109}$Pt, $^{119}$Sb, $^{189}$mOs, $^{192}$Ir, $^{219}$Rn, $^{215}$Po, $^{221}$Fr, $^{255}$Fm, $^{11}$C, $^{13}$N, $^{15}$O, $^{75}$Br, $^{198}$Au, $^{199}$Au, $^{224}$Ac, $^{77}$Br, $^{113}$mIn, $^{95}$Ru, $^{97}$Ru, $^{103}$Ru, $^{105}$Ru, $^{107}$Hg, $^{203}$Hg, $^{121}$mTe, $^{122}$mTe, $^{125}$mTe, $^{165}$Tm, $^{167}$Tm, $^{168}$Tm, $^{197}$Pt, $^{109}$Pd, $^{142}$Pr, $^{143}$Pr, $^{161}$Tb, $^{57}$Co, $^{58}$Co, $^{51}$Cr, $^{59}$Fe, $^{75}$Se, $^{201}$Tl, $^{76}$Br and $^{169}$Yb.

Use of the composition as described above for the manufacture of a medicament in prevention and/or treatment of an autoimmune disease, an immune response against transplant, an allergy, an infection, a neurodegenerative disease, or a tumor.

Preferably, the autoimmune disease is one or more selected from the group consisting of arthritis, rheumatoid arthritis, psoriasis, multiple sclerosis, ulcerative colitis, Crohn's disease, systemic lupus erythematosus, glomerulonephritis, dilatation cardiomyopathy-like disease, Sjogren's syndrome, allergic contact dermatitis, polymyositis, scleroderma, periarterial polyarteritis, rheumatic fever, vitiligo, insulin-dependent diabetes mellitus, Behcet's syndrome and chronic thyroiditis.

Preferably, the neurodegenerative disease is one or more selected from the group consisting of Parkinson's disease, Huntington's disease, Machado-Joseph disease, amyotrophic lateral sclerosis and Creutzfeldt-Jakob disease.

Preferably, the tumor is one or more selected from the group consisting of leukemia, lymphoma, myeloma, brain tumor, head and neck squamous cell carcinoma, non-small cell lung cancer, nasopharyngeal carcinoma, esophageal cancer, gastric cancer, pancreatic cancer, gallbladder cancer, liver cancer, colorectal cancer, breast cancer, ovarian cancer, cervical cancer, endometrial cancer, uterine sarcoma, prostate cancer, bladder cancer, renal cell carcinoma, and melanoma.

Use of the antibody and the functional the fragment thereof as described above for the manufacture of a medicament for preventing and/or treating of an autoimmune disease, an immune response against a transplant, an allergy, an infection, a neurodegenerative disease and a tumor.

A drug for preventing and/or treating of an autoimmune disease, an immune response against a transplant, an allergy, an infection, a neurodegenerative disease and a tumor, the drug comprises the antibody capable of specifically binding to PD-1 and the functional fragment capable of specifically binding to PD-1 thereof as described above, and pharmaceutically acceptable carrier;

Alternatively, the drug comprises the composition as described above and pharmaceutically acceptable carrier.

Herein, the term "pharmaceutically acceptable" means that the compound is physiologically acceptable when the compound is administered to a human, and does not cause an allergic reaction such as a gastrointestinal disorder, dizziness or other allergic reaction, or a systemic allergic reaction similar to these allergic reactions.

In the present disclosure, "pharmaceutically acceptable carrier" includes, but is not limited to, binders (such as microcrystalline cellulose, alginates, gelatin and polyvinylpyrrolidone), fillers (such as starch, sucrose, glucose and anhydrous lactic acid), disintegrants (such as cross-linked PVP, cross-linked carboxymethyl sodium starch, croscarmellose sodium and low-substituted hydroxypropyl cellulose), lubricants (magnesium stearate, aluminum stearate, talc, polyethylene glycol, sodium benzoate), wetting agent (such as glycerin), surfactants (such as cetyl alcohol), and absorption enhancers, flavoring agents, sweeteners, diluents, coating agents, etc.

Use of the antibody and the functional fragment thereof as described above in prevention and/or treatment of an autoimmune disease, an immune response against a transplant, an allergy, an infection, a neurodegenerative disease, or a tumor.

Preferably, the autoimmune disease is one or more selected from the group consisting of arthritis, rheumatoid arthritis, psoriasis, multiple sclerosis, ulcerative colitis, Crohn's disease, systemic lupus erythematosus, glomerulonephritis, dilatation cardiomyopathy-like disease, Sjogren's syndrome, allergic contact dermatitis, polymyositis, scleroderma, periarterial polyarteritis, rheumatic fever, vitiligo, insulin-dependent diabetes mellitus, Behcet's syndrome and chronic thyroiditis.

Preferably, the neurodegenerative disease is one or more selected from the group consisting of Parkinson's disease, Huntington's disease, Machado-Joseph disease, amyotrophic lateral sclerosis and Creutzfeldt-Jakob disease.

Preferably, the tumor is one or more selected from the group consisting of leukemia, lymphoma, myeloma, brain tumor, head and neck squamous cell carcinoma, non-small cell lung cancer, nasopharyngeal, carcinoma, esophageal cancer, gastric cancer, pancreatic cancer, gallbladder cancer, liver cancer, colorectal cancer, breast cancer, ovarian cancer, cervical cancer, endometrial cancer, uterine sarcoma, prostate cancer, bladder cancer, renal cell carcinoma, and melanoma.

A method of preventing and/or treating an autoimmune disease, an immune response against a transplant, an allergy, an infection, a neurodegenerative disease or a tumor, comprises administering the drug to a subject in need thereof.

Preferably, the above-mentioned individual is a human being.

BRIEF DESCRIPTION OF DRAWINGS

In order to more clearly illustrate the specific embodiments of the present disclosure or the technical solutions in the conventional art, the drawings used in the specific embodiments or the description of the conventional art will be briefly described below, and it is obvious that the drawings in the following description are some embodiments of the present disclosure and a person having ordinary skill in the art can obtain other drawings based on these drawings without any creative work.

DETAILED DESCRIPTION

Figure 1:
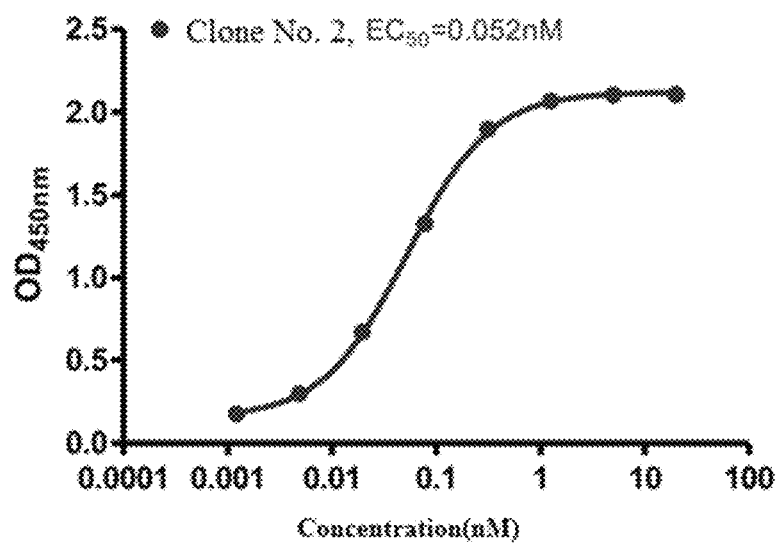
FIG. 1 shows the human PD-1 binding activity of the monoclonal antibody secreted by Clone No. 2 described in Example 1.

The embodiments of the present disclosure will be described in detail below with reference to the embodiments. However, a person having ordinary skill in the art will understand that the following embodiments are merely to illustrate present disclosure and are not intended to limit the scope of the disclosure. For those embodiments in which specific conditions are not specified, they were carried out according to the conventional conditions or the conditions recommended by the manufacturer. For those used reagents or instruments of which the manufacturers are not indicated, they were all commercially available conventional products.

Example 1

Preparation of Murine Anti-Human PD-1 Monoclonal Antibody 1.1. Immunization of Animal Female BALB/c mice, 6 to 8 weeks old, purchased from Beijing Huafukang Biotechnology Co., Ltd., were used as experimental animals. One week after the mice were acclimated to the environment, immunization began. For the initial immunization, 100 μg of recombinant human PD-1-Fc protein was thoroughly mixed with Freund's complete adjuvant (Sigma-Aldrich, Catalog Number F5881) to form an emulsion, which was intraperitoneally injected into the mice. Two weeks later, booster immunizations were performed. For the booster immunization, 50 μg of recombinant human PD-1-Fc protein was thoroughly mixed with Freund's incomplete adjuvant (Sigma-Aldrich, Catalog Number F5806) to form an emulsion, which was intraperitoneally injected into the mice. The immunization was boosted in the same way every 2 weeks, for a total 3 times. On the seventh day after the last immunization, blood was collected from retro orbital venous plexus of the mice and centrifuged to separate serum, and the antibody titer was determined by ELISA. Mice with high titers were selected for hybridization to make hybridomas. Three days before the hybridization, 50 μg of recombinant human PD-1-Fc protein was intraperitoneally injected into mice without adjuvant. On the day of hybridization, the spleen was aseptically removed to prepare a single spleen cell suspension for use.

1.2. Preparation of Hybridomas

Myeloma cells SP2/0 in logarithmic growth phase were centrifuged at 1,000 rpm for 5 minutes, the supernatant was discarded, and the cells were suspended in incomplete DMEM medium (Gibco, cat No. 11965) and counted. The cells needed were taken, washed twice with an incomplete culture medium. At the same time, a spleen cell suspension prepared from a mouse after immunization was washed twice with an incomplete culture medium. The myeloma cells and the spleen cells were mixed at a ratio of 1:10 or 1:5, and washed once with an incomplete culture medium in a 50 mL plastic centrifuge tube, and then centrifuged at 1,200 rpm for 8 minutes. The supernatant was discarded and a Pasteur pipette was used to remove residual liquid. The centrifuge tube was gently tapped on palm to make the precipitated cells loose and even, and then the tube was placed in 40° C. water bath to preheat. 1 mL of 45% PEG-4000 (pH 8.0, Sigma, cat No. P7181) preheated to 40° C. was added with 1 mL pipette at about 1 minute (with an optimum time of 45 seconds), stirred gently with a pipette when adding (stirred with a pipette), visible particles should be seen with the naked eyes. 20 to 30 mL of incomplete medium preheated to 37° C. was added to the tube with 10 mL pipette within 90 seconds to terminate PEG action, and allowed to stand at 20 to 37° C. for 10 minutes. The tube was centrifuged at 1,000 rpm for 5 minutes, and the supernatant was discarded. 5 mL of HAT medium (DMEM+HAT, Sigma, cat No. 1 H0262-10VL) was added, and the precipitated cells were mixed gently (remember not to blow vigorously so as not to separate the fused cells) to make a well mixed suspension. Additional HAT medium was added until 80 to 100 mL (the spleen cell concentration was made to be 1 to $2 \times 10^6$/mL). The suspension was dispensed into a 96-well cell culture plate, 0.1 mL per well; and a 24-well plate, 1.0 to 1.5 mL per well. The plates were incubated at 37° C. incubator with 6% $CO_2$. Generally, six 96-well plates were used. After 5 days, ½ medium was replaced with fresh HAT medium. After 7 to 10 days, the HAT medium was replaced with HT medium (DMEM+HT, Sigma cat No. H0137-10VL). The growth of hybridoma cells was observed routinely, and the supernatant was collected for antibody detection after the confluence of the cells reached 1/10 or more. The positive colonies were expanded and frozen.

1.3. Clone Screening and Identification

ELISA was used to screen anti-human PD-1 antibody from hybridoma culture supernatants. Recombinant human PD-1 (purchased from Sino Biological Inc., Catalog Number 10377-H08H) was coated on a 96-well high-absorbing ELISA plate with a carbonate buffer solution with pH 9.6, the coating concentration was 1 μg/mL, the coating amount was 100 μL per well, and the coating was carried out at 4° C. overnight. The plate was washed five times with PBST, blocked with 300 μL/well of PBST containing 1% BSA, and then incubated at 25° C. for 1 hour. The plate was washed five times with PBST. 100 μL culture supernatant samples and the positive serum control were added to each well respectively, and then the plated was incubated at 25° C. for 1 hour. The plate was washed five times with PBST. Then, 100 μL horseradish peroxidase-labeled anti-mouse IgG antibody (Abcam, Catalog Number Ab7068) 1:10,000 diluted in PBST containing 1% BSA was added to each well, and then the plated was incubated at 25° C. for 1 hour. The plate was washed five times with PBST. 100 μL/well of colorimetric substrate TMB was added and incubated at room temperature for 10 minutes. Color development was terminated by adding 100 μL/well of 1 M $H_2SO_4$. The absorbance at 450 nm was read on a microplate reader. Positive clones capable of producing anti-human PD-1 antibody were selected based on the reading value at OD 450 nm.

Whether the anti-human PD-1 antibodies produced by positive clones could block the binding of PD-1/PD-L1 was determined by ELISA. Recombinant human PD-1-Fc was coated on a 96-well high-absorbing ELISA plate with a carbonate buffer solution with pH 9.6, the coating concentration was 1 μg/mL, the coating amount was 100 μL per well, and the coating was carried out at 4° C. overnight. The plate was washed five times with PBST, blocked with 300 μL/well of PBST containing 1% BSA, and then incubated at 25° C. for 1 hour. The plate was washed five times with PBST. 50 μL anti-human PD-1 antibody sample and positive control were added to each well respectively, and then biotin-labeled PD-L1 was added at a concentration of 20 nM (final concentration 10 nM), 50 μL/well, and then incubated at 25° C. for 90 minutes. The plate was washed five times with PBST. Then, Streptavidin-HRP (BD Pharmingen, Catalog Number 554066) 1:1,000 diluted in PBST containing 1% BSA was added, 100 μL/well, and then incubated at 25° C. for 1 hour. The plate was washed five times with PBST. 100 μL/well of colorimetric substrate TMB was added and incubated at room temperature for 10 minutes. Color development was terminated by adding 100 μL/well of 1 M $H_2SO_4$. The absorbance at 450 nm was read on a microplate reader. The anti-human PD-1 antibody capable of inhibiting the biding of human PD-1-Fc/biotin-labeled PD-L1 was determined as having neutralization activity. Positive clones capable of producing anti-human PD-1 neutralization antibody were selected based on the blocking ability.

Figure 2:
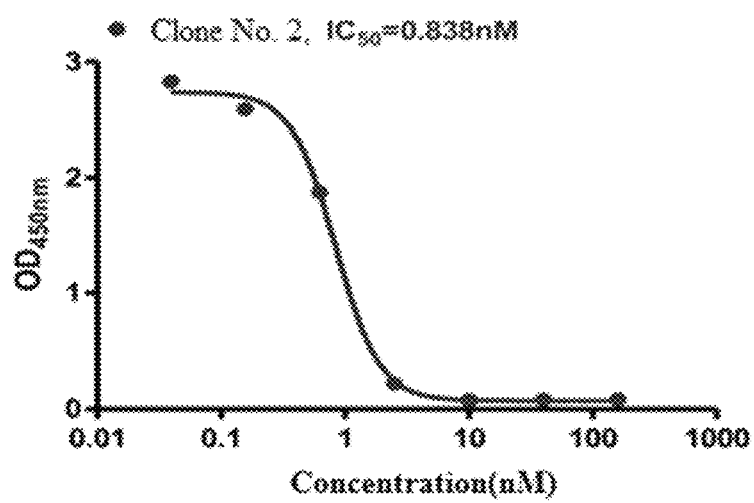
FIG. 2 shows the PD-1/PD-L1 blocking activity of the monoclonal antibody secreted by Clone No. 2 in Example 1.

As shown in FIG. 1, Clone No. 2 had strong human PD-1 binding activity; as shown in FIG. 2, Clone No. 2 also had pretty strong blocking activity against the binding of human PD-1/PD-L1.

1.4. Sequencing of Monoclonal Antibody

The clones having both antigen-binding activity and antigen-neutralization activity obtained by screening were subjected to sequencing of antibody DNA sequence. Cellular mRNA was first extracted using RNAprep Pure Kit (Tiangen, DP430). The steps were as follows: $1 \times 10^7$ cells were centrifuged at 300×g for 5 minutes and collected into a centrifuge tube, and all supernatant was carefully aspirated. The lysis step was carried out immediately. The bottom of the centrifuge tube was flicked to loose the cell pellet, 600 μL of lysis buffer RL was added and vortexed. All solution was transferred to a filtration column CS (the filtration column CS was placed in a collection tube), centrifuged at 12,000 rpm (~13,400×g) for 2 minutes, and the filtrate was collected. One fold volume of 70% ethanol (usually 350 μL or 600 μL) was added to the filtrate, well mixed, the obtained solution and precipitate were transferred into an adsorption column CR3 (the adsorption column CR3 was put into a collection tube), centrifuged at 12,000 rpm (~13,400×g) for 30 to 60 seconds, the liquid waste in the collection tube was removed, the adsorption column CR3 was put back into the collection tube. 350 μL of deproteinized solution RW1 was added to the adsorption column CR3, centrifuged at 12,000 rpm (~13,400×g) for 30 to 60 seconds, the liquid waste in the collection tube was removed, the adsorption column CR3 was put back into the collection tube. 80 μL of DNase I working solution was added to the center of the adsorption column CR3 and the column CR3 was allowed to stand at room temperature for 15 minutes. 350 µL of deproteinized solution RW1 was added to the adsorption column CR3, centrifuged at 12,000 rpm (~13,400×g) for 30 to 60 seconds, the liquid waste in the collection tube was removed, the adsorption column CR3 was put back into the collection tube. 500 µL of rinsing solution RW was added to the adsorption column CR3 (checked whether ethanol had been added before use), the column CR3 was allowed to stand at room temperature for 2 minutes, centrifuged at 12,000 rpm (~13,400×g) for 30 to 60 seconds, the liquid waste in the collection tube was removed, the adsorption column CR3 was put back into the collection tube. The column CR3 was centrifuged at 12,000 rpm (~13,400×g) for 2 minutes, and the waste was removed. The adsorption column CR3 was left at room temperature for a few minutes to let the residual rinsing solution in the adsorbent material thoroughly dry. The adsorption column CR3 was transferred into a new RNase-Free centrifuge tube, 30 to 100 µL of RNase-Free ddH$_2$O was added, the tube was allowed to stand at room temperature for 2 minutes, and then centrifuged at 12,000 rpm (~13,400×g) for 2 minutes to obtain a RNA solution.

The first strand of cDNA was synthesized using the QuantScript RT kit (Tiangen, KR103). The steps are as follows: the template RNA was thawed on ice; the primer, 10×RT mix (containing RNasin and DTT), Super pure dNTP mixture, RNase-Free ddH$_2$O were thawed at room temperature (15 to 25° C.), and placed on ice immediately after thawing. Each solution was well mixed by vortexer before use, the tube was centrifuged briefly to collect residual liquid on the side of the tube. Reverse transcription system mixture (Tiangen Bio Quant cDNA First-Strand Synthesis Kit, Catalog Number KR103-04; 10× Reverse Transcription Buffer 2 µL, Ultra-Pure dNTP 2 µL, Random Primer 2 µL, Reverse Transcription Enzyme 1 µL) was prepared according to Table 1. The mixture was mixed thoroughly, the duration of vortex was no more than 5 minutes; and then centrifuged briefly and placed on ice. Finally, the template RNA (50 ng to 2 µg) was added to the mixture, mixed thoroughly, the duration of vortex was no more than 5 seconds, centrifuged briefly to collect residual liquid on the sides of the tube, incubated at 37° C. for 60 minutes. The first strand of cDNA produced by reverse transcription was used for subsequent PCR reaction.

The primers used in the PCR reaction are as shown in Table 1.

```
VHprimer
F1:  GAGGTGAAGCTGCAGGAGTCAGGACCTAGCCTGGTG
R1:  AGGT(C/G)(A/C)AACTGCAG(C/G)AGTC(A/T)GG
R2:  AGGT(C/G)(A/C)AGCTGCAG(C/G)AGTC(A/T)GG
R3:  AGGT(C/G)CAGCTGCAG(C/G)AGTC(A/T)GG
R4:  CCAGGGGCCAGTGGATAGACAAGCTTGGGTGTCGTTTT
F2:  ATAGACAGATGGGGGTGTCGTTTTGGC
F3:  CTTGACCAGGCATCCTAGAGTCA
F4:  AGGGGCCAGTGGATAGACTGATGG
F5:  AGGGACCAAGGGATAGACAGATGG
R5:  (G/C)A(A/G)GT(A/T/C/G)(A/C)AGCTG(G/C)AG(G/C)
AGTC
R6:  (G/C)A(A/G)GT(A/T/C/G)(A/C)AGCTG(G/C)AG(G/C)
AGTC(A/T)GG VLprimer
R1:  GGTGATATCGTGAT(A/G)AC(C/A)CA(G/A)GATGAACTCTC
R2:  GGTGATATC(A/T)TG(A/C)TGACCCAA(A/T)CTCCACTCTC
R3:  GGTGATATCGT(G/T)CTCAC(C/T)CA(A/G)TCTCCAGCAAT
F1:  GGGAAGATGGATCCAGTTGGTGCAGCATCAGC
F2:  GGATACAGTTGGTGCAGCATC
R4:  GA(C/T)ATTGTG(A/C)T(G/C)AC(A/C)CA(A/G)(A/T)CT
(A/C)CA
```

When primers were used, any upstream primer of the VH primers could be used with any downstream primer; in the same way, any upstream primer of the VL primers could also be used with any downstream primer. The target band obtained by PCR amplification was cloned into the pGEM-T vector. A single clone was picked for DNA sequencing.

Example 2

Preparation of Chimeric Anti-Human PD-1 Monoclonal Antibody

The amino acid sequence of the light chain variable region of the antibody obtained by PCR amplification is set forth in SEQ ID NO: 10, and the amino acid sequence of the heavy chain variable region of antibody is set forth in SEQ ID NO: 14. The sequence of the complementarity-determining region can be obtained by excluding the sequence of the framework region from the mouse variable region sequence; wherein the amino acid sequences of the three complementarity-determining regions CDR-L1, CDR-L2, CDR-L3 of the light chain are set forth in SEQ ID NO: 1, 5 and 6, respectively; the amino acid sequences of the three complementarity-determining regions CDR-H1, CDR-H2, CDR-H3 of the heavy chain are set forth in SEQ ID NO: 7, 8 and 9, respectively. The above-mentioned variable region sequences were cloned into a eukaryotic expression vector X0GC, the amino acid sequence of the light chain constant region of the antibody is set forth in SEQ ID NO: 15, and the amino acid sequence of the heavy chain constant region of the antibody is set forth in SEQ ID NO: 16. The vectors expressing the antibody light chain (the full-length of the light chain was the light chain variable region of the antibody linked to SEQ ID NO: 15) and the heavy chain (the full-length of the heavy chain was the heavy chain variable region of antibody linked to SEQ ID NO: 16) were transfected into 293F cell line (FreeStyle™ 293-F Cells, Catalog Number R79007, Invitrogen). Cells were subcultured one day prior to transfection. Cells On the day of transfection, cells were harvested by centrifugation and then resuspended in fresh FreeStyle™ 293 Expression Medium (FreeStyle™ 293 Expression Medium, Catalog Number 12338001, Gibco) at a density of 200×10$^5$ cells/mL. Plasmids were added based on the transfection volume to a final concentration of 36.67 µg/mL, mixed gently; then linear PEI (polyethyleneimine, linear, M. W. 25000, Catalog Number 43896, Alfa Aesar) was added to a final concentration of 55 µg/mL, mixed gently. Thereafter, the cells were placed in a shaker at 120 rpm and incubated at 37° C. for 1 hour. 19-fold transfection volume of fresh medium was then added and the cells were continually cultured at 37° C. in a shaker at 120 rpm. The culture supernatant 5 to 6 days after transfection was collected by centrifugation.

Example 3

Binding Activity and Kinetics of Chimeric Anti-Human PD-1 Monoclonal Antibody

The binding activity of anti-human PD-1 chimeric monoclonal antibody to its antigen human PD-1 was determined by ELISA. Recombinant human PD-1 (purchased from Sino Biological Inc.) was coated on a 96-well high-absorbing ELISA plate with a carbonate buffer solution with pH 9.6, the coating concentration was 1 µg/mL, the coating amount was 100 µL per well, and the coating was carried out at 4° C. overnight. The plate was washed five times with PBST and blocked with 300 µL/well of PBST containing 1% BSA, and then incubated at 25° C. for 1 hour. The plate was washed five times with PBST. The monoclonal antibody control, Pembrolizumab, and the anti-human PD-1 chimeric monoclonal antibody samples serially diluted in PBST containing 1% BSA were added, 100 μL per well, incubated at 25° C. for 1 hour. The plate was washed five times with PBST. Then, horseradish peroxidase-labeled anti-human IgG antibody (Chemicon, Catalog Number AP309P) 1:2,000 diluted in PBST containing 1% BSA was added, 100 μL per well, incubated at 25° C. for 1 hour. The plate was washed five times with PBST. 100 μL/well of colorimetric substrate TMB was added and incubated at room temperature for 10 minutes. Color development was terminated by adding 100 μL/well of 1 M $H_2SO_4$. The absorbance at 450 nm was read on a microplate reader.

Figure 3:
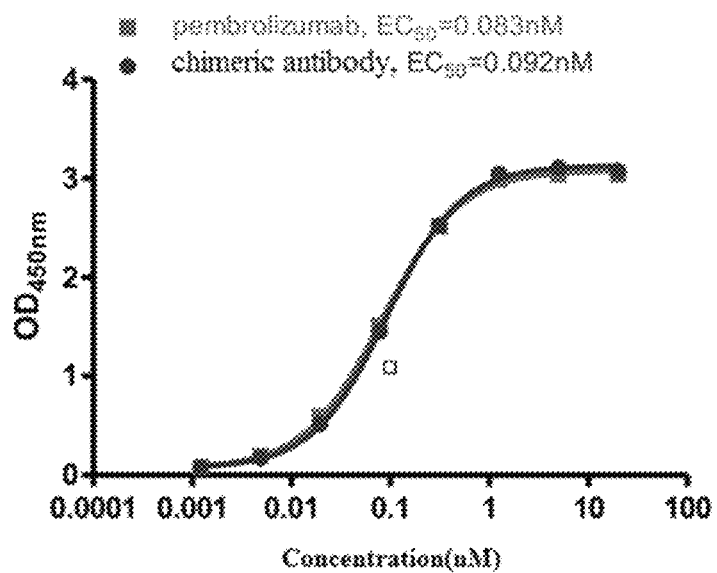
FIG. 3 shows the human PD-1 binding activity of the anti-human PD-1 chimeric monoclonal antibody in Example 3.

The result is as shown in FIG. 3, the anti-human PD-1 chimeric monoclonal antibody has good binding affinity to human PD-1, which is similar to the binding activity of Pembrolizumab.

The kinetics of anti-human PD-1 chimeric monoclonal antibody binding to its antigen human PD-1 was detected using Biacore™ X100. The instrument utilizes an optical surface plasmon resonance technique to detect association and dissociation between a molecule coupled on a sensor chip and an analyte. CM5 chips (GE Healthcare, BR-1000-12) were used. Brief experiment procedure was as follow: anti-human PD-1 chimeric antibody was diluted to 2 μg/mL with a running buffer (1 xHBS-EP+10 mM HEPES, 150 mM NaCl, 3 mM EDTA, 0.05% surfactant P20, pH 7.4), then injected at a rate of 10 μL/min onto a CM5 chip coupled with antihuman IgG, lasted for 60 seconds. In the association phase, the antigen PD-1 was diluted to multiple concentrations with a running buffer, and injected at a rate of 30 pL/min for 180 seconds. In the dissociation phase, the duration of the dissociation was 1,200 seconds. Glycine solution (GE Healthcare, BR-1003-54) was used to regenerate for 30 seconds at a speed of 10 μL/min. The experiment method for the control antibody was similar, except the duration of dissociation was adjusted to 600 seconds. Association rate constant and dissociation rate constant were analyzed and calculated by Biacore™ X100 evaluation software. See Table 2 for the association rate constant, dissociation rate constant and dissociation equilibrium constant of the anti-human PD-1 chimeric antibodies. The data demonstrates that, compared to Pembrolizumab, after binding to antigen PD-1, anti-human PD-1 chimeric monoclonal antibody could maintain the binding state for a longer time and is not easy to be dissociated, which contributes greatly to its biological functions.

TABLE 2

Binding Kinetics of Anti-Human PD-1 Chimeric Antibody to Human PD-1

| Sample | $K_{on}$ (1/Ms) | $K_{off}$ (1/s) | $K_D$ (nM) |
|---|---|---|---|
| Pembrolizumab | 3.731E+5 | 2.708E−3 | 7.257 |
| Anti-human PD-1 Chimeric Antibody | 2.150E+5 | 2.950E−4 | 1.372 |

Example 4

Species Specificity and Binding Specificity of Chimeric Anti-Human PD-1 Monoclonal Antibody The species specificity of the anti-human PD-1 chimeric monoclonal antibody was determined by ELISA. Recombinant human PD-1, monkey PD-1, rat PD-1 and mouse PD-1 (all purchased from Sino Biological Inc.), were coated on a 96-well high-absorbing ELISA plate with a carbonate buffer solution with pH 9.6, the coating concentration was 1 μg/mL, the coating amount was 100 μL per well, and the coating was carried out at 4° C. overnight. The plate was washed five times with PBST and blocked with 300 μL/well of PBST containing 1% BSA, and then incubated at 25° C. for 1 hour. The plate was washed five times with PBST. The control and the anti-human PD-1 chimeric monoclonal antibody sample serially diluted in PBST containing 1% BSA were added, 100 μL per well, incubated at 25° C. for 1 hour. The plate was washed five times with PBST. Then, horseradish peroxidase-labeled anti-human IgG antibody (Chemicon, Catalog Number AP309P) 1:2,000 diluted in PBST containing 1% BSA was added, 100 μL per well, incubated at 25° C. for 1 hour. The plate was washed five times with PBST. 100 μL/well of colorimetric substrate TMB was added and incubated at room temperature for 10 minutes. Color development was terminated by adding 100 μL/well of 1 M $H_2SO_4$: The absorbance at 450 nm was read on a microplate reader.

The binding specificity of the anti-human PD-1 chimeric monoclonal antibody was determined by ELISA. Recombinant human PD-1, CD28, CTLA4, ICOS, BTLA, PD-L1, PD-L2, CD80, CD86, B7-H2 (all purchased from Sino Biological Inc.), were coated on a 96-well high-absorbing ELISA plate with a carbonate buffer solution with pH 9.6, the coating concentration was 1 μg/mL, the coating amount was 100 μL per well, and the coating was carried at 4° C. out overnight. The plate was washed five times with PBST and blocked with 300 μL/well of PBST containing 1% BSA and incubated at 25° C. for 1 hour. The plate was washed five times with PBST. The control and the anti-human PD-1 chimeric monoclonal antibody sample diluted in PBST containing 1% BSA were added, 100 μL per well, incubated at 25° C. for 1 hour. The plate was washed five times with PBST. Then, horseradish peroxidase-labeled anti-human IgG antibody (Chemicon, Catalog Number AP309P) 1:2,000 diluted in PBST containing 1% BSA was added, 100 μL was added to each well, incubated at 25° C. for 1 hour. The plate was washed five times with PBST. 100 μL/well of colorimetric substrate TMB was added and incubated at room temperature for 10 minutes. Color development was terminated by adding 100 μL/well of 1 M $H_2SO_4$. The absorbance at 450 nm was read on a microplate reader.

Figure 4:
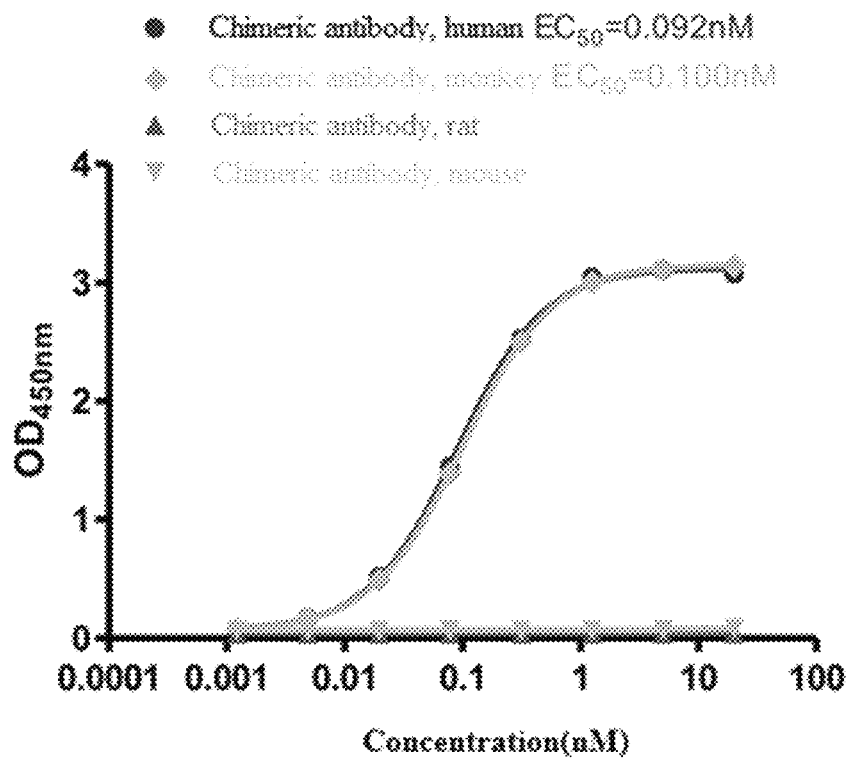
FIG. 4 shows the species specificity of the anti-human PD-1 chimeric monoclonal antibody in Example 4.
Figure 5:
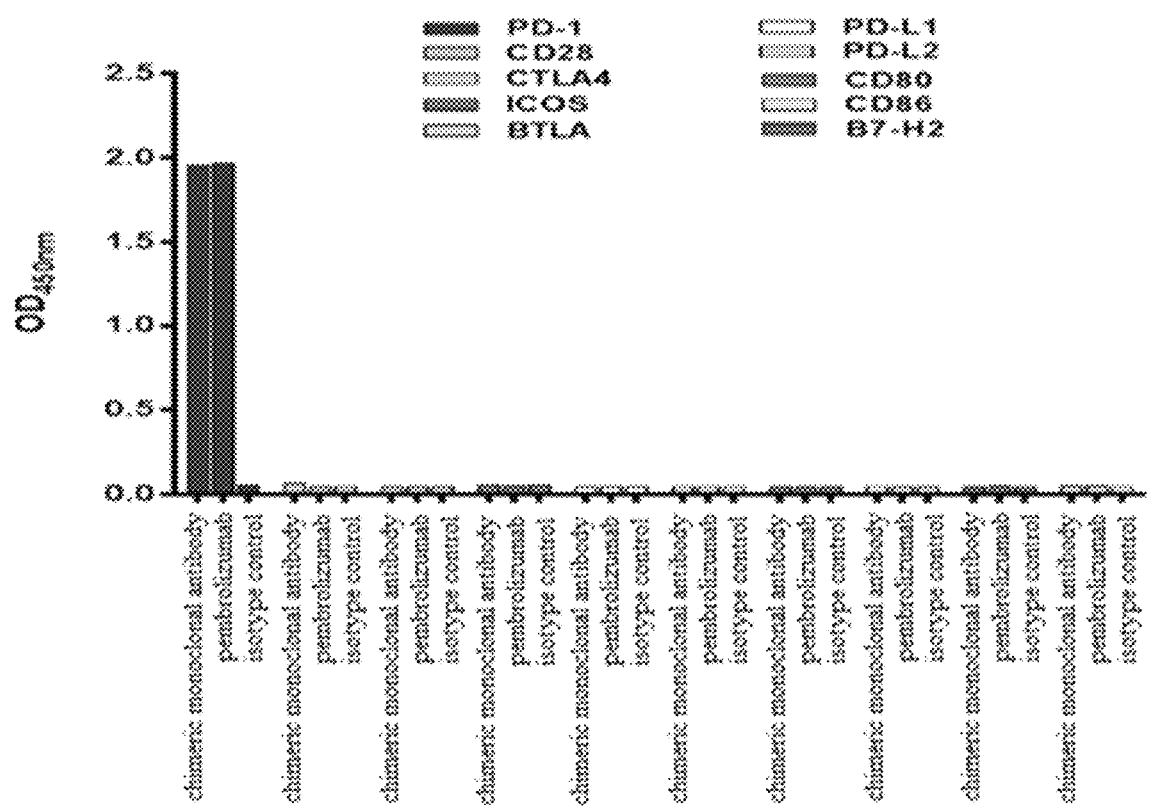
FIG. 5 shows the binding specificity of the anti-human PD-1 chimeric monoclonal antibody in Example 4.

The result is as shown in FIG. 4, the anti-human PD-1 chimeric monoclonal antibody could bind to human PD-1 and monkey PD-1 with similar affinity, but did not bind to rat and mouse PD-1, indicating that it is species-specific. In addition, as shown in FIG. 5, the anti-human PD-1 chimeric monoclonal antibody also has excellent binding specificity, which only binds to PD-1 but not other members of CD28 family or B7 family.

Example 5

PD-1 and Ligands Blocking Activity of Chimeric Anti-Human PD-1 Monoclonal Antibody Recombinant human PD-1-Fc was coated on a 96-well high-absorbing ELISA plate with a carbonate buffer solution with pH 9.6, the coating concentration was 1 μg/mL, the coating amount was 100 μL per well, and the coating was carried at 4° C. out overnight. The plate was washed five times with PBST and blocked with 300 μL/well of PBST containing 1% BSA and incubated at 25° C. for 1 hour. The plate was washed five times with PBST. The positive control and the anti-human PD-1 antibody sample were added, 50

µL per well. And then biotin-labeled PD-L1 was added at a concentration of 20 nM (final concentration 10 nM), or biotin-labeled PD-L2 at a concentration of 320 nM (final concentration 160 nM), 50 µL per well, incubated at 25° C. for 90 minutes. The plate was washed five times with PBST. Then, Streptavidin-HRP (BD Pharmingen, Catalog Number 554066) 1:1,000 diluted in PBST containing 1% BSA was added, 100 µL per well, incubated at 25° C. for 1 hour. The plate was washed five times with PBST. 100 µL/well of colorimetric substrate TMB was added and incubated at room temperature for 10 minutes. Color development was terminated by adding 100 µL/well of 1 M $H_2SO_4$. The absorbance at 450 nm was read on a microplate reader.

Figure 6:
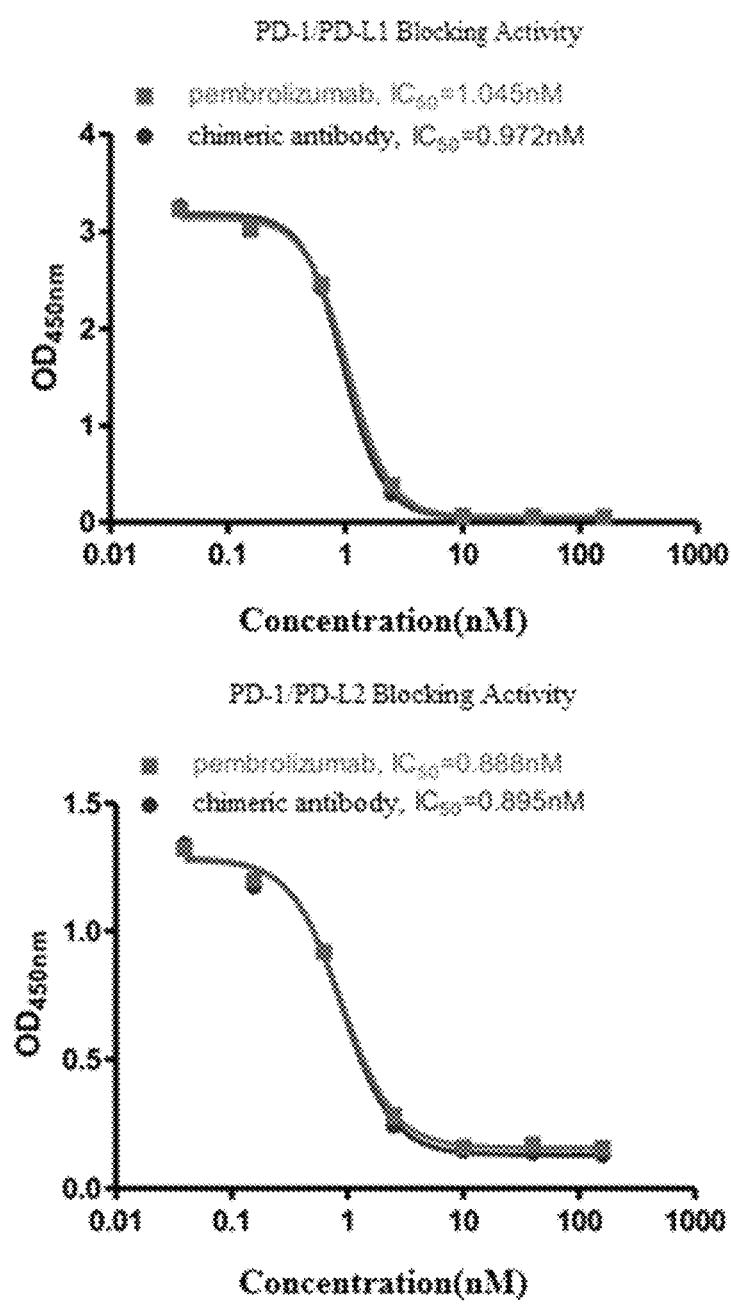
FIG. 6 shows the PD-1/PD-L1, PD-1/PD-L2 blocking activity of the anti-human PD-1 chimeric monoclonal antibody in Example 5.

The result is as shown in FIG. 6, the anti-human PD-1 chimeric monoclonal antibody has similar PD-1/PD-L1 and PD-1/PD-L2 blocking activity compared to that of Pembrolizumab.

Example 6

T Cell Function Regulatory Activity by Chimeric Anti-Human PD-1 Monoclonal Antibody The PBMC used in the experiment was purchased from Lonza, Catalog Number CC-2702.

Induction of DC cells with PBMC: PBMCs were resuscitated with complete medium (RPMI 1640+10% FBS), then washed once with serum-free medium; the cells were resuspended in serum-free medium, and seeded into a cell culture flask, and then incubated at 37° C. in an incubator with 5% $CO_2$. After 90 minutes, the non-adherent cells and medium were removed; the adherent monocytes were cultured in complete medium containing 100 ng/mL GM-CSF and 100 ng/mL IL-4, and the medium was changed after 3 days. After the cells were cultured for another 3 days, the medium was changed to complete medium containing 100 ng/mL GM-CSF, 100 ng/mL IL-4 and 20 ng/mL TNF-alpha and cultured for one more day to complete the induction of DC cells. T cells were isolated from another individual-derived PBMC: T cells were isolated using a Pan T Cell Isolation Kit from Miltenyi Biotech (Catalog Number 5150414820) followed the instructions for the specific experiment procedure. The induced mature DC cells were seeded into a 96-well plate, 10,000 cells per well, and isolated T cells were added, 100,000 cells per well; and then the sample to be tested was added and incubated for 120 hours together. At the end of the incubation, the supernatant was collected, and the levels of IL-2 and IFN-gamma (IFN-γ) were detected using an ELISA kit purchased from RayBiotech.

Figure 7:
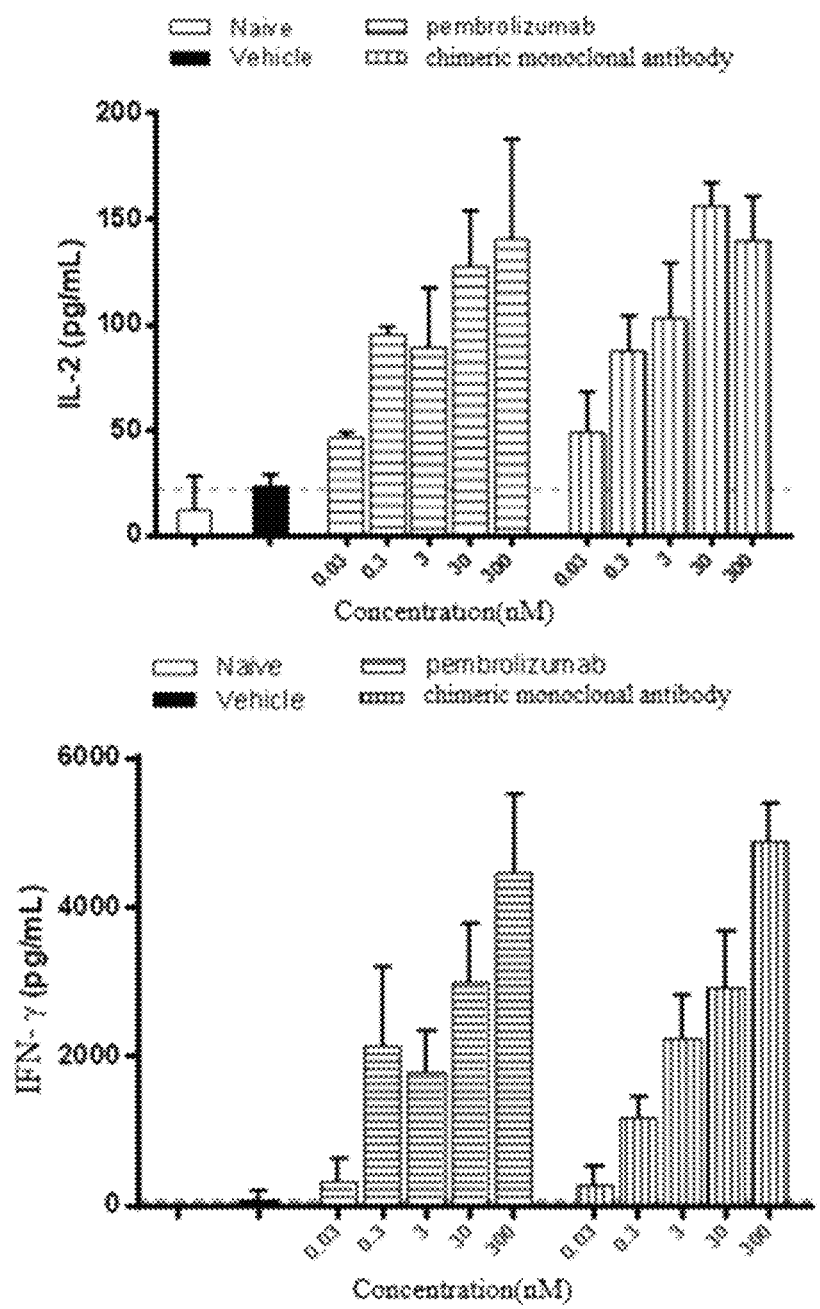
FIG. 7 shows the T cell function regulatory activity of the anti-human PD-1 chimeric monoclonal antibody in Example 6.

The result is as shown in FIG. 7, in the MLR system, the anti-human PD-1 chimeric monoclonal antibody enhanced the secretion of IL-2 and IFN-gamma (IFN-γ) and showed a similar effect on regulation of T cell functional activity compared to that of Pembrolizumab.

Example 7

Pharmacokinetics Study of Chimeric Anti-Human PD-1 Monoclonal Antibody in Rats

Female SD rats, 6 to 8 weeks old, purchased from Beijing Huafukang Biotechnology Co., Ltd., were used as experimental animals. One week after the rats were acclimated to the environment, the rats were randomly divided into groups, 3 rats per group. Anti-human PD-1 chimeric monoclonal antibody and control monoclonal antibody Pembrolizumab were administered respectively at a dose of 20 nmol/kg by intravenous injection, single dose. At 0, 5 minutes, 30 minutes, 1 hour, 4 hours, 8 hours, 24 hours, 48 hours, 72 hours, 96 hours, 120 hours, 168 hours, 216 hours, 264 hours, 312 hours after administration, the retro-orbital blood sample was collected without anticoagulation, and the blood sample was allowed to stand at room temperature for 30 minutes to 1 hour; after coagulation, the blood sample was centrifuged at 3,000 rpm for 10 minutes, the obtained serum sample was frozen at −80 OC and stored for testing.

The concentrations of anti-human PD-1 chimeric monoclonal antibody and control monoclonal antibody Pembrolizumab in the serum were determined by ELISA. Briefly, human recombinant PD-1 protein was coated on a high-absorbing ELISA plate with a carbonate buffer solution with pH 9.6 at 4° C. overnight. The plate was washed with PBST. To prevent non-specific binding, the plate was blocked with PBST containing 5% nonfat milk powder, and then washed with PBST. Then, the serum sample to be tested diluted with PBST containing 10% mixed rat serum and 1% BSA was added and incubated at 25° C. for 1 hour, and the plate was washed with PBST. Horseradish peroxidase-labeled anti-human IgG antibody (Chemicon, Catalog Number AP309P) diluted in PBST containing 5% skimmed milk powder was added, incubated at 25° C. for 1 hour, the then plate was washed with PBST. Finally, color development was carried out using the colorimetric substrate TMB at room temperature for 10 minutes. Color development was terminated by adding 100 µL/well of 1 M $H_2SO_4$. The absorbance at 450 nm was read on a microplate reader.

Figure 8:
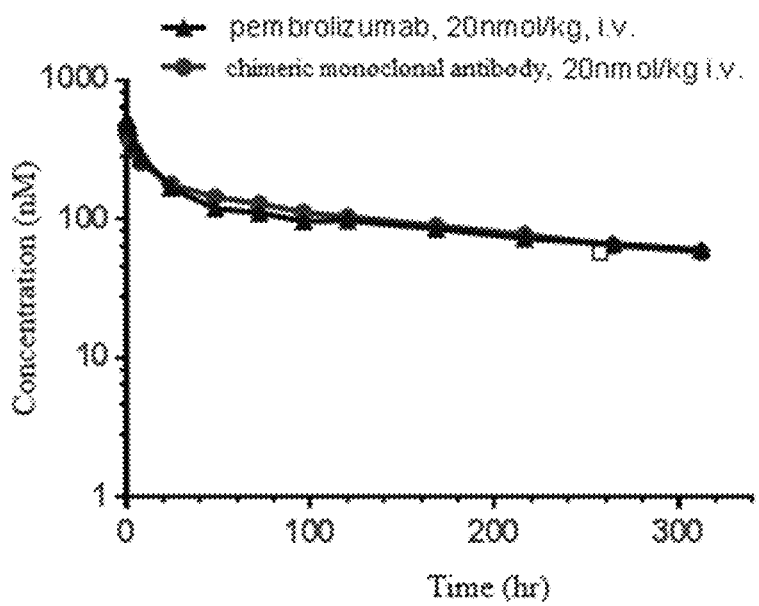
FIG. 8 shows the concentration-time curve of the anti-human PD-1 chimeric monoclonal antibody after a single intravenous injection in rat in Example 7.

The result is as shown in FIG. 8, a single intravenous injection dose of 20 nmol/kg of anti-human PD-1 chimeric monoclonal antibody or control monoclonal antibody Pembrolizumab showed similar concentration-time curves and pharmacokinetic features in rats. The pharmacological parameters of the anti-human PD-1 chimeric monoclonal antibody are as follows: half-life $t_{1/2}$ was 212 hours; the area under the concentration-time curve $AUC_{0-312\ hr}$ was 33967 nM·hr; the estimated initial concentration Co was 464 nM; the apparent volume of distribution Vd was 118 mL/kg; the clearance CL was 0.39 mL/hr/kg; the mean residence time $MRT_{last}$ was 119 hours.

Example 8

Antitumor Efficacy of Chimeric Anti-Human PD-1 Monoclonal Antibody in Vivo

The growth inhibitory effect of Chimeric Anti-human PD-1 monoclonal antibody on HCC827 tumor xenografts inoculated in PBMC humanized mice was detected in the present example.

NCG immunodeficient mice, female, 6-8 weeks old, purchased from Nanjing Galaxy BioPharma Co., Ltd., were used as experimental materials. One week after the mice were acclimated to the environment, each mouse was inoculated with $1 \times 10^7$ HCC827 human non-small cell lung cancer cells (purchased from the Basic Medical Cell Center of the Institute of Basic Medical Sciences, Chinese Academy of Medical Sciences). When the tumor size reached about 100 $mm^3$, the mice were divided into groups according to the tumor size, 6 mice per group, including a solvent control group, an anti-human PD-1 chimeric monoclonal antibody administration group and a Pembrolizumab administration group. Each mouse was intravenously injected $5 \times 10^6$ human PBMC cells to humanize the immune system, and then the solvent or antibody was administered according to the group design, the dose was 70 nmol/kg, i.p. The mice were administered twice a week for 3 weeks. From the day of administration, the tumor size was measured 3 times a week, longest diameter "a" and width "b" were measured, the tumor seize was calculated as: $(mm^3)=(a \times b^2)/2$.

Figure 9:
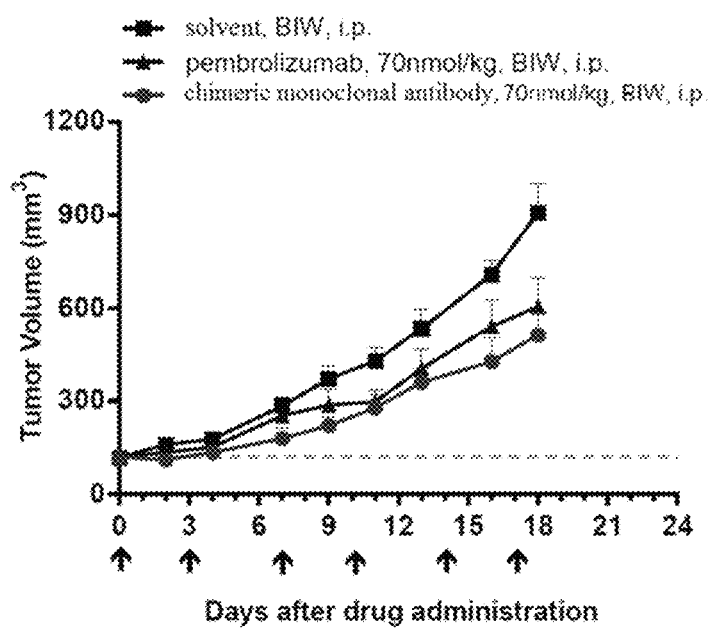
FIG. 9 shows an in vivo antitumor efficacy of the anti-human PD-1 chimeric monoclonal antibody in Example 8.

The result is as shown in FIG. 9, the anti-human PD-1 chimeric monoclonal antibody has antitumor activity and inhibited the growth of HCC827 non-small cell lung cancer graft in PBMC humanized mice, showing that it has comparable or slightly stronger anti-tumor efficacy compared to that of Pembrolizumab.

Example 9

Preparation of Humanized Anti-Human PD-1 Monoclonal Antibody

The humanized anti-human PD-1 monoclonal antibody was obtained according to the method of Leung et al. (Molecule Immunol, 1995, 32: 1413-27).

The humanized template that best matches murine antibody variable region sequence was selected from the Germline database. The template for the light chain variable region is IGKV3-11*01, the sequence is set forth in SEQ ID NO: 43; the template for the heavy chain variable region is IGHV3-23*04, and the sequence is set forth in SEQ ID NO: 44. The CDR regions of the selected human template were replaced by the murine antibody CDR regions. The obtained grafted humanized antibody light chain variable region has a sequence set forth in SEQ ID NO: 45, and the grafted humanized antibody heavy chain variable region has a sequence set forth in SEQ ID NO: 46. Sites on SEQ ID NO: 45 and SEQ ID NO: 46 were selected for back mutation and NQS site on the CDR1 region of SEQ ID NO: 45 was selected for mutation to remove possible glycosylation site. The obtained CDR-L1 sequence is set forth in SEQ ID NO: 2, or SEQ ID NO: 3, or ID NO: 4; the obtained light chain variable region sequence is set forth in SEQ ID NO: 25 to 36; the obtained heavy chain variable region sequence is set forth in SEQ ID NO: 37 to 42. The light chain variable region was linked to the light chain constant region (SEQ ID NO: 15) to obtain the corresponding full-length sequence of the light chain; the heavy chain variable region was linked to the heavy chain constant region (SEQ ID NO: 16) to obtain the corresponding full-length sequence of the heavy chain. The usable humanized sequence was obtained by affinity and stability screening. After affinity and stability screening, the obtained light chain and heavy chain variable region sequence information of humanized sequences are shown in Table 3.

TABLE 3

| VL | SEQ ID NO: |
|---|---|
| Chimeric Monoclonal Antibody | 10 |
| AH00290/AH00291/AH00296 | 25 |
| AH00293 | 26 |
| AH00294 | 27 |
| AH00295 | 28 |
| AH00298 | |
| AH00291-N26Q/AH00296-N26Q | 29 |
| AH00291-N26S/AH00296-N26S | 30 |
| AH00291-S28A/AH00296-S28A | 31 |
| AH00294-N26Q | 32 |
| AH00294-N26S | 33 |
| AH00294-S28A | 34 |
| BMIII | 35 |
| BMIV | 36 |

TABLE 3-continued

| VH | SEQ ID NO: |
|---|---|
| Chimeric Monoclonal Antibody | 14 |
| AH00290 | 37 |
| AH00291/AH00293/AH00298/ AH00291-N26Q/AH00291-N26S/ AH00291-S28A | 38 |
| AH00294/AH00294-N26Q/ AH00294-N26S/AH00294-S28A | 39 |
| AH00295/AH00296/AH00296-N26Q/ AH00296-N26S/AH00296-S28A | 40 |
| BMIII | 41 |
| BMIV | 42 |

Example 10

Biological Activity of Humanized Anti-Human PD-1 Monoclonal Antibody in Vitro

The in vitro biological activity of humanized anti-human PD-1 monoclonal antibody was determined, including binding activity to human PD-1 and the blocking activity against the binding of PD-1/PD-L1. The humanized sequences to be tested included: AH00290, AH00291, AH00293, AH00294, AH00295, AH00296, AH00298, BM III, BM IV, AH00290-N26Q, AH00291-N26S, AH00291-S28A, AH00294-N26Q, AH00294-N26S, AH00294-S28A, AH00296-N26Q, AH00296-N26S, AH00296-S28A; the method of determination was ELISA, and the specific experiment procedure was the same as the method of determining chimeric anti-human PD-1 monoclonal antibody.

The experiment result is shown in Table 4. Compared to the above-mentioned chimeric anti-human PD-1 monoclonal antibody, all of the tested humanized sequences maintained pretty good activity, showing strong PD-1 binding activity and blocking activity against the binding of PD-1/PD-L1.

TABLE 4

PD-1 Binding Activity and the Blocking Activity against the Binding of PD-1/PD-L1 of Anti-human PD-1 Humanized Antibody

| Sample | PD-1 Binding Activity ($EC_{50}$, nM) | PD-1/PD-L1 Blocking Activity ($IC_{50}$, nM) |
|---|---|---|
| Chimeric monoclonal antibody | 0.031 | 1.453 |
| AH00290 | 0.024 | 1.086 |
| AH00291 | 0.025 | 1.105 |
| AH00293 | 0.026 | 1.201 |
| AH00294 | 0.032 | 1.350 |
| AH00295 | 0.025 | 1.188 |
| AH00296 | 0.027 | 1.207 |
| AH00298 | 0.028 | 1.215 |
| BMIII | 0.034 | 1.197 |
| BMIV | 0.028 | 1.298 |
| AH00291-N26Q | 0.046 | 1.569 |
| AH00291-N26S | 0.039 | 1.431 |
| AH00291-S28A | 0.042 | 1.361 |
| AH00294-N26Q | 0.041 | 1.491 |
| AH00294-N26S | 0.043 | 1.479 |
| AH00294-S28A | 0.047 | 1.464 |
| AH00296-N26Q | 0.044 | 1.274 |
| AH00296-N26S | 0.037 | 1.066 |
| AH00296-S28A | 0.048 | 1.755 |

Example 11

Detection of Purity and Thermal Stability of Humanized Anti-Human PD-1 Monoclonal Antibody by Size-Exclusion High-Performance Liquid Chromatography (SE-HPLC)

TSKgel SuperSW3000 chromatography column (Catalog Number: 0018675) was used. The mobile phase was 0.1 mol/l of phosphate buffer (NaH$_2$PO$_4$—Na$_2$HPO$_4$), 0.1 mol/l of sodium sulfate buffer, pH 6.7; the flow rate was 0.35 mL/min; the column temperature was 25° C.; sample pool temperature was 4° C.; detection wavelength was 280 nm. The sample was diluted with sample buffer to 1 mg/mL, and the injection volume was 5 μL. The experiment result was processed by Agilent High Performance Liquid Chromatograph 1260 System Workstation, and purity was calculated by the percentage of the main peak using area normalization method. The humanized anti-human PD-1 monoclonal antibody prepared above was subjected to SE-HPLC purity assay. To determine the thermal stability of these monoclonal antibodies, the samples were placed under high temperature conditions of 40° C., and the samples were subjected to SE-HPLC assay at week 2 and week 4 respectively to observe thermal stability, and the result is as shown in Table 5 below. All of the humanized anti-human PD-1 antibodies showed good and considerable stability except AH00296-S28A.

TABLE 5

Thermal Stability of Humanized Anti-human PD-1 Monoclonal Antibody at 40° C. by SE-HPLC

| Humanized Anti-human PD-1 Monoclonal Antibody | SE-HPLC Purity (%) | | |
|---|---|---|---|
| | T = 0 | Week 2 | Week 4 |
| BMIII | 99.23 | 98.16 | 95.78 |
| BMIV | 98.19 | 98.42 | 94.80 |
| AH00290 | 98.97 | 98.04 | 94.73 |
| AH00291 | 99.30 | 98.22 | 95.87 |
| AH00293 | 97.79 | 96.55 | 94.32 |
| AH00294 | 98.77 | 97.68 | 96.52 |
| AH00295 | 99.24 | 98.16 | 96.17 |
| AH00296 | 99.63 | 98.55 | 96.73 |
| AH00298 | 99.34 | 98.13 | 95.87 |
| AH00291-N26Q | 98.55 | 98.56 | 97.90 |
| AH00291-N26S | 99.05 | 99.08 | 98.50 |
| AH00291-S28A | 98.95 | 98.89 | 98.40 |
| AH00294-N26Q | 99.14 | 99.08 | 98.64 |
| AH00294-N26S | 99.23 | 99.19 | 98.64 |
| AH00294-S28A | 99.30 | 99.33 | 98.69 |
| AH00296-N26Q | 99.10 | 99.10 | 98.27 |
| AH00296-N26S | 99.60 | 99.59 | 98.96 |
| AH00296-S28A | 99.70 | 84.38 | 62.42 |

Example 12

Determination of Tm Value of Humanized Anti-Human PD-1 Monoclonal Antibody

The melting temperature (Tm) of the humanized anti-human PD-1 monoclonal antibody was determined by Differential Scanning Fluorimetry (DSF). DSF is a method for detecting the thermal denaturation process of proteins in a sample by using the fluorescence intensity change of the fluorescent indicator to determine the protein denaturation temperature. The reagent used was SYPRO Orange Protein Fluorescent Dye (Sigma-Aldrich, USA, Catalog Number S5692; 5000× concentration, in DMSO). AB 7500 Real Time PCR machine was purchased from Applied Biosystems, Inc., USA. The protein fluorescent dye was diluted 1:50 with sample buffer, and 1 L of the diluted dye was mixed with 19 μL of protein solution, so the final dilution of the fluorescent dye was 1:1,000. The diluted fluorescent dye was added to a 96-well plate, and three parallel wells were set for each sample. The plate was sealed with an optical sealing film, centrifuged at 1,000 rpm for 2 minutes to remove air bubbles. The RT-PCR program was set as follows: melting curve was set in continuous mode, scanning temperature range was 25 to 99° C., heating rate was 1% (about 1° C./min), and then 25° C. for 2 min. Data was collected during heating, the reporter group was set as "ROX", the quenching group was set as "None", and the reaction volume was 20 μL. The sample concentration was 1 mg/mL, and the reference solution was sample buffer. Fluorescence curves and the first derivative were plotted using Protein Thermal Shift™ Software v1.3 software. In the DSF test, the midpoint temperature of the first transition of the protein is usually considered as the denaturation temperature of the thermal stability of the protein. The Tm values of the humanized anti-human PD-1 monoclonal antibody were measured and the result is as shown in Table 6 below. All of the humanized anti-human PD-1 monoclonal antibodies have pretty good Tm value.

TABLE 6

Tm Value of Humanized Anti-human PD-1 Monoclonal Antibody

| Humanized Anti-human PD-1 Monoclonal Antibody | Tm Value |
|---|---|
| BMIII | 70.7° C. |
| BMIV | 65.2° C. |
| AH00290 | 66.5° C. |
| AH00291 | 67.7° C. |
| AH00293 | 69.1° C. |
| AH00294 | 67.9° C. |
| AH00295 | 70.5° C. |
| AH00296 | 70.0° C. |
| AH00298 | 67.9° C. |
| AH00291-N26Q | 68.5° C. |
| AH00291-N26S | 67.8° C. |
| AH00291-S28A | 68.8° C. |
| AH00294-N26Q | 66.6° C. |
| AH00294-N26S | 65.9° C. |
| AH00294-S28A | 68.4° C. |
| AH00296-N26Q | 67.6° C. |
| AH00296-N26S | 70.1° C. |
| AH00296-S28A | 69.1° C. |

Example 13

Detection of Charge Isomers of Humanized Anti-Human PD-1 Monoclonal Antibody by Cation Exchange Chromatography (CEX)

Cation exchange chromatography column MabPac SCX-10 was used, 4 mm×250 mm (Catalog Number: 78655). 20 mmol/l of 2-(N-morpholine) ethanesulfonic acid (MES) (pH 5.6) and 60 mmol/l of sodium chloride were used as mobile phase A; 20 mmol/l of MES (pH 5.6) and 300 mmol/l of sodium chloride were used as mobile phase B. The flow rate was 0.5 mL/min; the column temperature was 25° C.; sample pool temperature was 4° C.; detection wavelength was 280 nm; the sample loading volume was 50 μL (1 mg/mL); the elution was carried out in a linear gradient from 5 to 50% over 60 minutes. The experiment result was processed by Agilent High Performance Liquid Chromatograph 1260 System Workstation, and the percentage of the peak area was calculated by the area normalization method. The humanized anti-human PD-1 monoclonal antibodies were subjected to CEX detection. To determine the chemical stability of these monoclonal antibodies, the above samples were put under high temperature conditions of 40° C., and the samples were taken out at week 2 and week 4 respectively for CEX detection and the changes in the proportion of charge variants was observed. The result is as shown in Table 7. All of the humanized anti-human PD-1 antibodies have a relatively low proportion of charge variants except AH00296-S28A.

TABLE 7

Changes in Charge Variants of Humanized Anti-human PD-1 Monoclonal Antibody at 40° C. by CEX

| Sample | Changes in Charge Variants | | | | | |
|---|---|---|---|---|---|---|
| | T = 0 | | | Week 2 | | |
| | Main Peak (%) | Acidic Peak (%) | Basic Peak (%) | Main Peak (%) | Acidic Peak (%) | Basic Peak (%) |
| BMIII | 68.2 | 18.2 | 13.6 | 64.0 | 22.8 | 13.2 |
| BMIV | 64.9 | 21.1 | 14.0 | 58.0 | 27.1 | 14.9 |
| AH00290 | 65.6 | 20.1 | 14.3 | 61.5 | 25.8 | 12.7 |
| AH00291 | 66.6 | 20.0 | 13.4 | 61.5 | 24.8 | 13.7 |
| AH00293 | 69.2 | 20.7 | 10.1 | 62.6 | 26.7 | 10.7 |
| AH00294 | 68.4 | 17.8 | 13.8 | 63.5 | 22.3 | 14.2 |
| AH00295 | 65.8 | 17.3 | 16.9 | 59.1 | 24.8 | 16.1 |
| AH00296 | 66.9 | 19.3 | 13.8 | 59.7 | 25.2 | 15.1 |
| AH00298 | 66.1 | 19.4 | 14.5 | 62.7 | 22.2 | 15.1 |
| AH00291-N26Q | 77.2 | 8.8 | 14.0 | 73.8 | 10.8 | 15.4 |
| AH00291-N26S | 77.6 | 8.2 | 14.2 | 71.6 | 11.4 | 17.0 |
| AH00291-S28A | 74.6 | 8.5 | 16.9 | 71.9 | 10.4 | 17.9 |
| AH00294-N26Q | 74.9 | 7.7 | 17.4 | 71.1 | 10.8 | 18.1 |
| AH00294-N26S | 78.0 | 7.7 | 14.3 | 73.2 | 11.2 | 15.6 |
| AH00294-S28A | 77.9 | 7.2 | 14.9 | 73.8 | 7.2 | 14.9 |
| AH00296-N26Q | 78.8 | 7.4 | 13.8 | 72.6 | 12.4 | 14.9 |
| AH00296-N26S | 76.9 | 7.3 | 15.8 | 70.6 | 12.6 | 16.8 |
| AH00296-S28A | 78.1 | 7.4 | 14.5 | 54.2 | 22.9 | 23.0 |

Finally, it should be understood that the above embodiments are only used to illustrate the technical solution of the present disclosure instead of limiting it; although the present disclosure has been described in detail with reference to the foregoing embodiments, it should be understood by those having ordinary skill in the art that the technical solutions described in the foregoing embodiments may be modified, or some or all of the technical features may be equivalently replaced; and the modifications or replacements, however, would not make the substances of the corresponding technical solutions depart from the scope of the technical solutions of the embodiments of the present disclosure.

Industrial Applicability: the antibody and functional fragment thereof provided by the present disclosure can specifically bind to PD-1, and can be used for preventing and/or treating of an autoimmune disease (for example, arthritis, rheumatoid arthritis, psoriasis, multiple sclerosis, ulcerative colitis, Crohn's disease, systemic lupus erythematosus, glomerulonephritis, dilatation cardiomyopathy-like disease, Sjogren's syndrome, allergic contact dermatitis, polymyositis, scleroderma, periarterial polyarteritis, rheumatic fever, vitiligo, insulin-dependent diabetes mellitus, Behcet's syndrome and chronic thyroiditis), an immune response against a transplant, an allergy, an infection, a neurodegenerative disease (for example, Parkinson's disease, Huntington's disease, Machado-Joseph disease, amyotrophic lateral sclerosis, Creutzfeldt-Jakob disease) and a tumor (for example, leukemia, lymphoma, myeloma, brain tumor, head and neck squamous cell carcinoma, non-small cell lung cancer, nasopharyngeal carcinoma, esophageal cancer, gastric cancer, pancreatic cancer, gallbladder cancer, liver cancer, colorectal cancer, breast cancer, ovarian cancer, cervical cancer, endometrial cancer, uterine sarcoma, prostate cancer, bladder cancer, renal cell carcinoma, and melanoma), etc.

The invention claimed is:

1. An antibody capable of specifically binding to PD-1 or a functional fragment thereof, wherein the antibody or the functional fragment thereof comprises a light chain variable region and a heavy chain variable region;
the light chain variable region comprises a light chain CDR consisting of CDR-L1, CDR-L2 and CDR-L3; the heavy chain variable region comprises a heavy chain CDR consisting of CDR-H1, CDR-H2 and CDR-H3;
the amino acid sequences of the CDR-L1, CDR-L2, and CDR-L3 are respectively set forth in SEQ ID NO: 1, 5 and 6, or respectively set forth in SEQ ID NO: 2, 5 and 6, or respectively set forth in SEQ ID NO: 3, 5 and 6, or respectively set forth in SEQ ID NO: 4, 5 and 6; and the amino acid sequences of the CDR-H1, CDR-H2, and CDR-H3 are respectively set forth in SEQ ID NO: 7, 8 and 9.

2. The antibody or the functional fragment thereof according to claim 1, wherein the antibody comprises a constant region sequence of any one selected from the group consisting of human IgG1, IgG2, IgG3, IgG4, IgA, IgM, IgE and IgD.

3. The antibody or the functional fragment thereof according to claim 1, wherein the functional fragment is selected from the group consisting of a F(ab')$_2$, a Fab', a Fab, and a Fv fragment, or wherein said antibody is an scFv antibody.

4. The antibody or the functional fragment thereof according to claim 1, wherein the amino acid sequences of light chain variable region and heavy chain variable region are respectively set forth in SEQ ID NO: 10 and SEQ ID NO: 14, or respectively set forth in SEQ ID NO: 11 and SEQ ID NO: 14, or respectively set forth in SEQ ID NO: 12 and SEQ ID NO: 14, or respectively set forth in SEQ ID NO: 13 and SEQ ID NO: 14.

5. The antibody or the functional fragment thereof according to claim 1, wherein light chain framework region of the light chain variable region comprises FR-L1, FR-L2, FR-L3 and FR-L4, and heavy chain framework region of the heavy chain variable region comprises FR-H1, FR-H2, FR-H3 and FR-H4;

the FR-L1 is selected from the amino acid sequence set forth in SEQ ID NO: 17 and the amino acid sequence set forth in SEQ ID NO: 17 but having one or more of the following substitutions:
the 1$^{st}$ amino acid D is replaced by E;
the 2$^{nd}$ amino acid V is replaced by I;
the 13$^{th}$ amino acid L is replaced by Y; and
the 19$^{th}$ amino acid A is replaced by V;
the FR-L2 is selected from the amino acid sequence set forth in SEQ ID NO: 18 and the amino acid sequence set forth in SEQ ID NO: 18 but having one or more of the following substitutions:
the 6$^{th}$ amino acid P is replaced by S;
the 7$^{th}$ amino acid G is replaced by H; and
the 9$^{th}$ amino acid A is replaced by S;
the FR-L3 is selected from the amino acid sequence set forth in SEQ ID NO: 19 and the amino acid sequence set forth in SEQ ID NO: 19 but having one or more of the following substitutions:
the 22$^{nd}$ amino acid L is replaced by V;
the 24$^{th}$ amino acid P is replaced by T;
the 28$^{th}$ amino acid A is replaced by G; and
the 31$^{st}$ amino acid F is replaced by Y;
the FR-L4 is selected from the amino acid sequence set forth in SEQ ID NO: 20 and the amino acid sequence set forth in SEQ ID NO: 20 but having the 7th amino acid Y replaced by L;
the FR-H1 has the amino acid sequence set forth in SEQ ID NO: 21;
the FR-H2 is selected from the amino acid sequence set forth in SEQ ID NO: 22 and the amino acid sequence set forth in SEQ ID NO: 22 but having one or more of the following substitutions:
the 5$^{th}$ amino acid A is replaced by T; and
the 14$^{th}$ amino acid A is replaced by S;
the FR-H3 is selected from the amino acid sequence set forth in SEQ ID NO: 23 and the amino acid sequence set forth in SEQ ID NO: 23 but having one or more of the following substitutions:
the 12$^{th}$ amino acid N is replaced by T;
the 14$^{th}$ amino acid Y is replaced by H; and
the 18$^{th}$ amino acid N is replaced by S; and
the FR H4 has the amino acid sequence set forth in SEQ ID NO: 24.

6. An isolated nucleic acid molecule selected from:
A) DNA or RNA, encoding the antibody or the functional fragment thereof according to claim 1; and
B) a nucleic acid complementary to the nucleic acid as defined in A).

7. A composition, comprising the antibody or the functional fragment thereof according to claim 1.

8. The composition according to claim 7, wherein the antibody or the functional fragment thereof is coupled to at least one diagnostic agent and/or therapeutic agent to form an immunoconjugate.

9. The composition according to claim 8, wherein the at least one diagnostic agent is selected from the group consisting of a radionuclide, a radioactive contrast agent, a paramagnetic ion, a metal, a fluorescent label, a chemiluminescent label, an ultrasound contrast agent, and a photosensitizer.

10. The composition according to claim 8, wherein the at least one therapeutic agent is selected from the group consisting of a naked antibody, a cytotoxic agent, a drug, a radionuclide, a boron atom, an immunomodulator, an anti-apoptotic agent, a photosensitizing therapeutic, an immunoconjugate and an oligonucleotide.

11. A method of treating one or more tumors in a subject, comprising administering the composition according to claim 7 to the subject:
wherein the one or more tumors is selected from the group consisting of leukemia, lymphoma, myeloma, brain tumor, head and neck squamous cell carcinoma, non-small cell lung cancer, nasopharyngeal carcinoma, esophageal cancer, gastric cancer, pancreatic cancer, gallbladder cancer, liver cancer, colorectal cancer, breast cancer, ovarian cancer, cervical cancer, endometrial cancer, uterine sarcoma, prostate cancer, bladder cancer, renal cell carcinoma, and melanoma.

12. A method of treating one or more tumors in a subject, comprising administering the antibody or the functional fragment thereof according to claim 1 to the subject:
wherein the one or more tumors is selected from the group consisting of leukemia, lymphoma, myeloma, brain tumor, head and neck squamous cell carcinoma, non-small cell lung cancer, nasopharyngeal carcinoma, esophageal cancer, gastric cancer, pancreatic cancer, gallbladder cancer, liver cancer, colorectal cancer, breast cancer, ovarian cancer, cervical cancer, endometrial cancer, uterine sarcoma, prostate cancer, bladder cancer, renal cell carcinoma, and melanoma.

13. A drug for treatment of one or more tumors, comprising the antibody or the functional fragment thereof according to claim 1, and a pharmaceutically acceptable carrier;
wherein the one or more tumors is selected from the group consisting of leukemia, lymphoma, myeloma, brain tumor, head and neck squamous cell carcinoma, non-small cell lung cancer, nasopharyngeal carcinoma, esophageal cancer, gastric cancer, pancreatic cancer, gallbladder cancer, liver cancer, colorectal cancer, breast cancer, ovarian cancer, cervical cancer, endometrial cancer, uterine sarcoma, prostate cancer, bladder cancer, renal cell carcinoma, and melanoma.

14. A method of treating one or more tumors in a subject, comprising administering the drug according to claim 13 to the subject.

15. The antibody or functional fragment thereof according to claim 1, wherein said antibody is a humanized antibody.

16. The antibody or functional fragment thereof according to claim 1, wherein said antibody is a chimeric antibody.

17. The antibody or functional fragment thereof according to claim 1, wherein said antibody is a bispecific antibody.

18. The antibody or the functional fragment thereof according to claim 1, wherein the amino acid sequences of light chain variable region and heavy chain variable region are respectively set forth in SEQ ID NO: 15 and SEQ ID NO: 16.

19. The antibody or the functional fragment thereof according to claim 5, wherein the light chain variable region comprises SEQ ID NO: 25 and the heavy chain variable region sequence comprises SEQ ID NO: 37.

20. The antibody or the functional fragment thereof according to claim 5, wherein the light chain variable region comprises SEQ ID NO: 25 and the heavy chain variable region sequence comprises SEQ ID NO: 38.

21. The antibody or the functional fragment thereof according to claim 5, wherein the light chain variable region comprises SEQ ID NO: 29 and the heavy chain variable region sequence comprises SEQ ID NO: 38.

22. The antibody or the functional fragment thereof according to claim 5, wherein the light chain variable region comprises SEQ ID NO: 30 and the heavy chain variable region sequence comprises SEQ ID NO: 38.

23. The antibody or the functional fragment thereof according to claim 5, wherein the light chain variable region comprises SEQ ID NO: 31 and the heavy chain variable region sequence comprises SEQ ID NO: 38.

24. The antibody or the functional fragment thereof according to claim 5, wherein the light chain variable region comprises SEQ ID NO: 26 and the heavy chain variable region sequence comprises SEQ ID NO: 38.

25. The antibody or the functional fragment thereof according to claim 5, wherein the light chain variable region comprises SEQ ID NO: 28 and the heavy chain variable region sequence comprises SEQ ID NO: 40.

26. The antibody or the functional fragment thereof according to claim 5, wherein the light chain variable region comprises SEQ ID NO: 25 and the heavy chain variable region sequence comprises SEQ ID NO: 40.

27. The antibody or the functional fragment thereof according to claim 5, wherein the light chain variable region comprises SEQ ID NO: 29 and the heavy chain variable region sequence comprises SEQ ID NO: 40.

28. The antibody or the functional fragment thereof according to claim 5, wherein the light chain variable region comprises SEQ ID NO: 30 and the heavy chain variable region sequence comprises SEQ ID NO: 40.

29. The antibody or the functional fragment thereof according to claim 5, wherein the light chain variable region comprises SEQ ID NO: 31 and the heavy chain variable region sequence comprises SEQ ID NO: 40.

30. The antibody or the functional fragment thereof according to claim 5, wherein the light chain variable region comprises SEQ ID NO: 28 and the heavy chain variable region sequence comprises SEQ ID NO: 38.

31. The antibody or the functional fragment thereof according to claim 5, wherein the light chain variable region comprises SEQ ID NO: 27 and the heavy chain variable region sequence comprises SEQ ID NO: 39.

32. The antibody or the functional fragment thereof according to claim 5, wherein the light chain variable region comprises SEQ ID NO: 32 and the heavy chain variable region sequence comprises SEQ ID NO: 39.

33. The antibody or the functional fragment thereof according to claim 5, wherein the light chain variable region comprises SEQ ID NO: 33 and the heavy chain variable region sequence comprises SEQ ID NO: 39.

34. The antibody or the functional fragment thereof according to claim 5, wherein the light chain variable region comprises SEQ ID NO: 34 and the heavy chain variable region sequence comprises SEQ ID NO: 39.

35. The antibody or the functional fragment thereof according to claim 5, wherein the light chain variable region comprises SEQ ID NO: 35 and the heavy chain variable region sequence comprises SEQ ID NO: 41.

36. The antibody or the functional fragment thereof according to claim 5, wherein the light chain variable region comprises SEQ ID NO: 36 and the heavy chain variable region sequence comprises SEQ ID NO: 42.

37. The antibody or the functional fragment thereof according to claim 5, wherein the antibody or functional fragment thereof comprises a light chain constant region comprising SEQ ID NO: 15 and a heavy chain constant region comprising SEQ ID NO: 16.

* * * * *

SEQUENCE LISTING

```
<160> NUMBER OF SEQ ID NOS: 46

<210> SEQ ID NO 1
<211> LENGTH: 11
<212> TYPE: PRT
<213> ORGANISM: Artificial
<220> FEATURE:
<223> OTHER INFORMATION: CDR-L1

<400> SEQUENCE: 1

Arg Ala Asn Gln Ser Ile Ser Asn Asn Leu His
1               5                   10

<210> SEQ ID NO 2
<211> LENGTH: 11
<212> TYPE: PRT
<213> ORGANISM: Artificial
<220> FEATURE:
<223> OTHER INFORMATION: CDR-L1

<400> SEQUENCE: 2

Arg Ala Gln Gln Ser Ile Ser Asn Asn Leu His
1               5                   10

<210> SEQ ID NO 3
<211> LENGTH: 11
<212> TYPE: PRT
<213> ORGANISM: Artificial
```

<220> FEATURE:
<223> OTHER INFORMATION: CDR-L1

<400> SEQUENCE: 3

Arg Ala Ser Gln Ser Ile Ser Asn Asn Leu His
1               5                   10

<210> SEQ ID NO 4
<211> LENGTH: 11
<212> TYPE: PRT
<213> ORGANISM: Artificial
<220> FEATURE:
<223> OTHER INFORMATION: CDR-L1

<400> SEQUENCE: 4

Arg Ala Asn Gln Ala Ile Ser Asn Asn Leu His
1               5                   10

<210> SEQ ID NO 5
<211> LENGTH: 7
<212> TYPE: PRT
<213> ORGANISM: Artificial
<220> FEATURE:
<223> OTHER INFORMATION: CDR-L2

<400> SEQUENCE: 5

Phe Ala Ser Gln Ser Ile Ser
1               5

<210> SEQ ID NO 6
<211> LENGTH: 9
<212> TYPE: PRT
<213> ORGANISM: Artificial
<220> FEATURE:
<223> OTHER INFORMATION: CDR-L3

<400> SEQUENCE: 6

Gln Gln Ser Asp Asn Trp Pro Leu Thr
1               5

<210> SEQ ID NO 7
<211> LENGTH: 10
<212> TYPE: PRT
<213> ORGANISM: Artificial
<220> FEATURE:
<223> OTHER INFORMATION: CDR-H1

<400> SEQUENCE: 7

Gly Phe Thr Phe Ser Ser Tyr Gly Met Ser
1               5                   10

<210> SEQ ID NO 8
<211> LENGTH: 17
<212> TYPE: PRT
<213> ORGANISM: Artificial
<220> FEATURE:
<223> OTHER INFORMATION: CDR-H2

<400> SEQUENCE: 8

Ser Ile Ser Gly Gly Gly Arg Tyr Thr Tyr Tyr Pro Asp Ser Met Lys
1               5                   10                  15

Gly

<210> SEQ ID NO 9
<211> LENGTH: 8
<212> TYPE: PRT

```
<213> ORGANISM: Artificial
<220> FEATURE:
<223> OTHER INFORMATION: CDR-H3

<400> SEQUENCE: 9

Glu Tyr Phe Tyr Thr Met Asp Tyr
1               5

<210> SEQ ID NO 10
<211> LENGTH: 107
<212> TYPE: PRT
<213> ORGANISM: Artificial
<220> FEATURE:
<223> OTHER INFORMATION: Light chain variable region

<400> SEQUENCE: 10

Asp Ile Val Leu Thr Gln Ser Pro Ala Thr Leu Ser Val Thr Pro Gly
1               5                   10                  15

Asp Ser Val Ser Leu Ser Cys Arg Ala Asn Gln Ser Ile Ser Asn Asn
            20                  25                  30

Leu His Trp Tyr Gln Gln Arg Ser His Glu Ser Pro Arg Leu Leu Ile
        35                  40                  45

Arg Phe Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asp Asn Trp Pro Leu
                85                  90                  95

Thr Phe Gly Ala Gly Thr Lys Leu Glu Ile Lys
            100                 105

<210> SEQ ID NO 11
<211> LENGTH: 107
<212> TYPE: PRT
<213> ORGANISM: Artificial
<220> FEATURE:
<223> OTHER INFORMATION: Light chain variable region

<400> SEQUENCE: 11

Asp Ile Val Leu Thr Gln Ser Pro Ala Thr Leu Ser Val Thr Pro Gly
1               5                   10                  15

Asp Ser Val Ser Leu Ser Cys Arg Ala Gln Gln Ser Ile Ser Asn Asn
            20                  25                  30

Leu His Trp Tyr Gln Gln Arg Ser His Glu Ser Pro Arg Leu Leu Ile
        35                  40                  45

Arg Phe Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asp Asn Trp Pro Leu
                85                  90                  95

Thr Phe Gly Ala Gly Thr Lys Leu Glu Ile Lys
            100                 105

<210> SEQ ID NO 12
<211> LENGTH: 107
<212> TYPE: PRT
<213> ORGANISM: Artificial
<220> FEATURE:
<223> OTHER INFORMATION: Light chain variable region
```

-continued

<400> SEQUENCE: 12

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Arg Ser His Glu Ser Pro Arg Leu Leu Ile
        35                  40                  45

Arg Phe Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asp Asn Trp Pro Leu
                85                  90                  95

Thr Phe Gly Ala Gly Thr Lys Leu Glu Ile Lys
            100                 105

<210> SEQ ID NO 13
<211> LENGTH: 107
<212> TYPE: PRT
<213> ORGANISM: Artificial
<220> FEATURE:
<223> OTHER INFORMATION: Light chain variable region

<400> SEQUENCE: 13

Asp Ile Val Leu Thr Gln Ser Pro Ala Thr Leu Ser Val Thr Pro Gly
1               5                   10                  15

Asp Ser Val Ser Leu Ser Cys Arg Ala Asn Gln Ala Ile Ser Asn Asn
            20                  25                  30

Leu His Trp Tyr Gln Gln Arg Ser His Glu Ser Pro Arg Leu Leu Ile
        35                  40                  45

Arg Phe Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asp Asn Trp Pro Leu
                85                  90                  95

Thr Phe Gly Ala Gly Thr Lys Leu Glu Ile Lys
            100                 105

<210> SEQ ID NO 14
<211> LENGTH: 117
<212> TYPE: PRT
<213> ORGANISM: Artificial
<220> FEATURE:
<223> OTHER INFORMATION: Heavy chain variable region

<400> SEQUENCE: 14

Glu Val Gln Leu Gln Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Glu Lys Arg Leu Glu Trp Val
        35                  40                  45

Ala Ser Ile Ser Gly Gly Gly Arg Tyr Thr Tyr Tyr Pro Asp Ser Met
    50                  55                  60

Lys Gly Arg Phe Thr Ile Ser Arg Asp Asn Ala Lys Asn Asn Leu His
65                  70                  75                  80

```
Leu Gln Met Ser Ser Leu Arg Ser Glu Asp Thr Ala Leu Tyr Tyr Cys
                85                  90                  95

Val Tyr Glu Tyr Phe Tyr Thr Met Asp Tyr Trp Gly Gln Gly Thr Ser
            100                 105                 110

Val Thr Val Ser Ser
        115

<210> SEQ ID NO 15
<211> LENGTH: 107
<212> TYPE: PRT
<213> ORGANISM: Artificial
<220> FEATURE:
<223> OTHER INFORMATION: Light chain constant region

<400> SEQUENCE: 15

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 16
<211> LENGTH: 327
<212> TYPE: PRT
<213> ORGANISM: Artificial
<220> FEATURE:
<223> OTHER INFORMATION: Heavy chain constant region

<400> SEQUENCE: 16

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160
```

```
Gly Val Glu Val His Asn Ala Lys Thr Lys Pro Arg Glu Glu Gln Phe
            165                 170                 175

Asn Ser Thr Tyr Arg Val Val Ser Val Leu Thr Val Leu His Gln Asp
        180                 185                 190

Trp Leu Asn Gly Lys Glu Tyr Lys Cys Lys Val Ser Asn Lys Gly Leu
    195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 17
<211> LENGTH: 23
<212> TYPE: PRT
<213> ORGANISM: Artificial
<220> FEATURE:
<223> OTHER INFORMATION: Light chain framework region FR-L1

<400> SEQUENCE: 17

Asp Val Val Leu Thr Gln Ser Pro Ala Thr Leu Ser Leu Ser Pro Gly
1               5                   10                  15

Glu Arg Ala Thr Leu Ser Cys
            20

<210> SEQ ID NO 18
<211> LENGTH: 15
<212> TYPE: PRT
<213> ORGANISM: Artificial
<220> FEATURE:
<223> OTHER INFORMATION: Light chain framework region FR-L2

<400> SEQUENCE: 18

Trp Tyr Gln Gln Lys Pro Gly Gln Ala Pro Arg Leu Leu Ile Arg
1               5                   10                  15

<210> SEQ ID NO 19
<211> LENGTH: 32
<212> TYPE: PRT
<213> ORGANISM: Artificial
<220> FEATURE:
<223> OTHER INFORMATION: Light chain framework region FR-L3

<400> SEQUENCE: 19

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Phe Cys
            20                  25                  30
```

<210> SEQ ID NO 20
<211> LENGTH: 10
<212> TYPE: PRT
<213> ORGANISM: Artificial
<220> FEATURE:
<223> OTHER INFORMATION: Light chain framework region FR-L4

<400> SEQUENCE: 20

Phe Gly Gly Gly Thr Lys Val Glu Ile Lys
1               5                   10

<210> SEQ ID NO 21
<211> LENGTH: 25
<212> TYPE: PRT
<213> ORGANISM: Artificial
<220> FEATURE:
<223> OTHER INFORMATION: Heavy chain framework region FR-H1

<400> SEQUENCE: 21

Glu Val Asn Leu Val Glu Ser Gly Gly Leu Val Gln Pro Gly Gly
1               5                   10                  15

Ser Leu Arg Leu Ser Cys Ala Ala Ser
            20                  25

<210> SEQ ID NO 22
<211> LENGTH: 14
<212> TYPE: PRT
<213> ORGANISM: Artificial
<220> FEATURE:
<223> OTHER INFORMATION: Heavy chain framework region FR-H2

<400> SEQUENCE: 22

Trp Val Arg Gln Ala Pro Gly Lys Gly Leu Glu Trp Val Ala
1               5                   10

<210> SEQ ID NO 23
<211> LENGTH: 32
<212> TYPE: PRT
<213> ORGANISM: Artificial
<220> FEATURE:
<223> OTHER INFORMATION: Heavy chain framework region FR-H3

<400> SEQUENCE: 23

Arg Phe Thr Ile Ser Arg Asp Asn Ser Lys Asn Asn Leu Tyr Leu Gln
1               5                   10                  15

Met Asn Ser Leu Arg Ala Glu Asp Thr Ala Val Tyr Tyr Cys Val Tyr
            20                  25                  30

<210> SEQ ID NO 24
<211> LENGTH: 11
<212> TYPE: PRT
<213> ORGANISM: Artificial
<220> FEATURE:
<223> OTHER INFORMATION: Heavy chain framework region FR-H4

<400> SEQUENCE: 24

Trp Gly Gln Gly Thr Leu Val Thr Val Ser Ser
1               5                   10

<210> SEQ ID NO 25
<211> LENGTH: 107
<212> TYPE: PRT
<213> ORGANISM: Artificial
<220> FEATURE:
<223> OTHER INFORMATION: Light chain variable region

```
<400> SEQUENCE: 25

Asp Ile Val Leu Thr Gln Ser Pro Ala Thr Leu Ser Leu Ser Pro Gly
1               5                   10                  15

Glu Arg Ala Thr Leu Ser Cys Arg Ala Asn Gln Ser Ile Ser Asn Asn
            20                  25                  30

Leu His Trp Tyr Gln Gln Lys Pro Gly Gln Ala Pro Arg Leu Leu Ile
        35                  40                  45

Arg Phe Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Phe Cys Gln Gln Ser Asp Asn Trp Pro Leu
                85                  90                  95

Thr Phe Gly Gly Gly Thr Lys Val Glu Ile Lys
            100                 105

<210> SEQ ID NO 26
<211> LENGTH: 107
<212> TYPE: PRT
<213> ORGANISM: Artificial
<220> FEATURE:
<223> OTHER INFORMATION: Light chain variable region

<400> SEQUENCE: 26

Asp Ile Val Leu Thr Gln Ser Pro Ala Thr Leu Ser Leu Ser Pro Gly
1               5                   10                  15

Glu Arg Ala Thr Leu Ser Cys Arg Ala Asn Gln Ser Ile Ser Asn Asn
            20                  25                  30

Leu His Trp Tyr Gln Gln Lys Pro Gly Gln Ala Pro Arg Leu Leu Ile
        35                  40                  45

Arg Phe Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asp Asn Trp Pro Leu
                85                  90                  95

Thr Phe Gly Gly Gly Thr Lys Val Glu Ile Lys
            100                 105

<210> SEQ ID NO 27
<211> LENGTH: 107
<212> TYPE: PRT
<213> ORGANISM: Artificial
<220> FEATURE:
<223> OTHER INFORMATION: Light chain variable region

<400> SEQUENCE: 27

Asp Val Val Leu Thr Gln Ser Pro Ala Thr Leu Ser Leu Ser Pro Gly
1               5                   10                  15

Glu Arg Ala Thr Leu Ser Cys Arg Ala Asn Gln Ser Ile Ser Asn Asn
            20                  25                  30

Leu His Trp Tyr Gln Gln Lys Pro Gly Gln Ala Pro Arg Leu Leu Ile
        35                  40                  45

Arg Phe Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80
```

Glu Asp Phe Ala Val Tyr Phe Cys Gln Gln Ser Asp Asn Trp Pro Leu
                85                  90                  95

Thr Phe Gly Gly Gly Thr Lys Val Glu Ile Lys
            100                 105

<210> SEQ ID NO 28
<211> LENGTH: 107
<212> TYPE: PRT
<213> ORGANISM: Artificial
<220> FEATURE:
<223> OTHER INFORMATION: Light chain variable region

<400> SEQUENCE: 28

Glu Val Val Leu Thr Gln Ser Pro Ala Thr Leu Ser Leu Ser Pro Gly
1               5                   10                  15

Glu Arg Ala Thr Leu Ser Cys Arg Ala Asn Gln Ser Ile Ser Asn Asn
                20                  25                  30

Leu His Trp Tyr Gln Gln Lys Pro Gly Gln Ala Pro Arg Leu Leu Ile
            35                  40                  45

Arg Phe Ala Ser Gln Ser Ile Ser Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Phe Cys Gln Gln Ser Asp Asn Trp Pro Leu
                85                  90                  95

Thr Phe Gly Gly Gly Thr Lys Val Glu Ile Lys
            100                 105

<210> SEQ ID NO 29
<211> LENGTH: 107
<212> TYPE: PRT
<213> ORGANISM: Artificial
<220> FEATURE:
<223> OTHER INFORMATION: Light chain variable region

<400> SEQUENCE: 29

Asp Ile Val Leu Thr Gln Ser Pro Ala Thr Leu Ser Leu Ser Pro Gly
1               5                   10                  15

Glu Arg Ala Thr Leu Ser Cys Arg Ala Gln Gln Ser Ile Ser Asn Asn
                20                  25                  30

Leu His Trp Tyr Gln Gln Lys Pro Gly Gln Ala Pro Arg Leu Leu Ile
            35                  40                  45

Arg Phe Ala Ser Gln Ser Ile Ser Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Phe Cys Gln Gln Ser Asp Asn Trp Pro Leu
                85                  90                  95

Thr Phe Gly Gly Gly Thr Lys Val Glu Ile Lys
            100                 105

<210> SEQ ID NO 30
<211> LENGTH: 107
<212> TYPE: PRT
<213> ORGANISM: Artificial
<220> FEATURE:
<223> OTHER INFORMATION: Light chain variable region

<400> SEQUENCE: 30

Asp Ile Val Leu Thr Gln Ser Pro Ala Thr Leu Ser Leu Ser Pro Gly

```
                1               5                  10                 15
Glu Arg Ala Thr Leu Ser Cys Arg Ala Ser Gln Ser Ile Ser Asn Asn
                20                 25                 30

Leu His Trp Tyr Gln Gln Lys Pro Gly Gln Ala Pro Arg Leu Leu Ile
            35                 40                 45

Arg Phe Ala Ser Gln Ser Ile Ser Gly Ile Pro Ala Arg Phe Ser Gly
            50                 55                 60

Ser Gly Ser Gly Thr Asp Phe Thr Leu Thr Ile Ser Ser Leu Glu Pro
65                 70                 75                 80

Glu Asp Phe Ala Val Tyr Phe Cys Gln Gln Ser Asp Asn Trp Pro Leu
                85                 90                 95

Thr Phe Gly Gly Gly Thr Lys Val Glu Ile Lys
                100                105

<210> SEQ ID NO 31
<211> LENGTH: 107
<212> TYPE: PRT
<213> ORGANISM: Artificial
<220> FEATURE:
<223> OTHER INFORMATION: Light chain variable region

<400> SEQUENCE: 31

Asp Ile Val Leu Thr Gln Ser Pro Ala Thr Leu Ser Leu Ser Pro Gly
1               5                  10                 15

Glu Arg Ala Thr Leu Ser Cys Arg Ala Asn Gln Ala Ile Ser Asn Asn
                20                 25                 30

Leu His Trp Tyr Gln Gln Lys Pro Gly Gln Ala Pro Arg Leu Leu Ile
            35                 40                 45

Arg Phe Ala Ser Gln Ser Ile Ser Gly Ile Pro Ala Arg Phe Ser Gly
            50                 55                 60

Ser Gly Ser Gly Thr Asp Phe Thr Leu Thr Ile Ser Ser Leu Glu Pro
65                 70                 75                 80

Glu Asp Phe Ala Val Tyr Phe Cys Gln Gln Ser Asp Asn Trp Pro Leu
                85                 90                 95

Thr Phe Gly Gly Gly Thr Lys Val Glu Ile Lys
                100                105

<210> SEQ ID NO 32
<211> LENGTH: 107
<212> TYPE: PRT
<213> ORGANISM: Artificial
<220> FEATURE:
<223> OTHER INFORMATION: Light chain variable region

<400> SEQUENCE: 32

Asp Val Val Leu Thr Gln Ser Pro Ala Thr Leu Ser Leu Ser Pro Gly
1               5                  10                 15

Glu Arg Ala Thr Leu Ser Cys Arg Ala Gln Gln Ser Ile Ser Asn Asn
                20                 25                 30

Leu His Trp Tyr Gln Gln Lys Pro Gly Gln Ala Pro Arg Leu Leu Ile
            35                 40                 45

Arg Phe Ala Ser Gln Ser Ile Ser Gly Ile Pro Ala Arg Phe Ser Gly
            50                 55                 60

Ser Gly Ser Gly Thr Asp Phe Thr Leu Thr Ile Ser Ser Leu Glu Pro
65                 70                 75                 80

Glu Asp Phe Ala Val Tyr Phe Cys Gln Gln Ser Asp Asn Trp Pro Leu
                85                 90                 95
```

```
Thr Phe Gly Gly Gly Thr Lys Val Glu Ile Lys
            100                 105

<210> SEQ ID NO 33
<211> LENGTH: 107
<212> TYPE: PRT
<213> ORGANISM: Artificial
<220> FEATURE:
<223> OTHER INFORMATION: Light chain variable region

<400> SEQUENCE: 33

Asp Val Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Arg Phe Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Phe Cys Gln Gln Ser Asp Asn Trp Pro Leu
                85                  90                  95

Thr Phe Gly Gly Gly Thr Lys Val Glu Ile Lys
            100                 105

<210> SEQ ID NO 34
<211> LENGTH: 107
<212> TYPE: PRT
<213> ORGANISM: Artificial
<220> FEATURE:
<223> OTHER INFORMATION: Light chain variable region

<400> SEQUENCE: 34

Asp Val Val Leu Thr Gln Ser Pro Ala Thr Leu Ser Leu Ser Pro Gly
1               5                   10                  15

Glu Arg Ala Thr Leu Ser Cys Arg Ala Asn Gln Ala Ile Ser Asn Asn
            20                  25                  30

Leu His Trp Tyr Gln Gln Lys Pro Gly Gln Ala Pro Arg Leu Leu Ile
        35                  40                  45

Arg Phe Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Phe Cys Gln Gln Ser Asp Asn Trp Pro Leu
                85                  90                  95

Thr Phe Gly Gly Gly Thr Lys Val Glu Ile Lys
            100                 105

<210> SEQ ID NO 35
<211> LENGTH: 107
<212> TYPE: PRT
<213> ORGANISM: Artificial
<220> FEATURE:
<223> OTHER INFORMATION: Light chain variable region

<400> SEQUENCE: 35

Asp Val Val Leu Thr Gln Ser Pro Ala Thr Leu Ser Val Ser Pro Gly
1               5                   10                  15

Glu Arg Val Thr Leu Ser Cys Arg Ala Asn Gln Ser Ile Ser Asn Asn
```

```
                    20                  25                  30
Leu His Trp Tyr Gln Gln Lys Pro Gly Gln Ser Pro Arg Leu Leu Ile
            35                  40                  45

Arg Phe Ala Ser Gln Ser Ile Ser Gly Ile Pro Ala Arg Phe Ser Gly
        50                  55                  60

Ser Gly Ser Gly Thr Asp Phe Thr Leu Thr Ile Ser Ser Val Glu Pro
65                  70                  75                  80

Glu Asp Phe Gly Val Tyr Phe Cys Gln Gln Ser Asp Asn Trp Pro Leu
                85                  90                  95

Thr Phe Gly Gly Gly Thr Lys Leu Glu Ile Lys
            100                 105

<210> SEQ ID NO 36
<211> LENGTH: 107
<212> TYPE: PRT
<213> ORGANISM: Artificial
<220> FEATURE:
<223> OTHER INFORMATION: Light chain variable region

<400> SEQUENCE: 36

Asp Val Val Leu Thr Gln Ser Pro Ala Thr Leu Ser Val Ser Pro Gly
1               5                   10                  15

Glu Arg Val Thr Leu Ser Cys Arg Ala Asn Gln Ser Ile Ser Asn Asn
            20                  25                  30

Leu His Trp Tyr Gln Gln Lys Ser His Gln Ser Pro Arg Leu Leu Ile
        35                  40                  45

Arg Phe Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Val Glu Thr
65                  70                  75                  80

Glu Asp Phe Gly Val Tyr Phe Cys Gln Gln Ser Asp Asn Trp Pro Leu
                85                  90                  95

Thr Phe Gly Gly Gly Thr Lys Leu Glu Ile Lys
            100                 105

<210> SEQ ID NO 37
<211> LENGTH: 117
<212> TYPE: PRT
<213> ORGANISM: Artificial
<220> FEATURE:
<223> OTHER INFORMATION: Heavy chain variable region

<400> SEQUENCE: 37

Glu Val Asn Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ser Ser Ile Ser Gly Gly Arg Tyr Thr Tyr Tyr Pro Asp Ser Met
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Tyr Glu Tyr Phe Tyr Thr Met Asp Tyr Trp Gly Gln Gly Thr Leu
            100                 105                 110
```

<210> SEQ ID NO 38
<211> LENGTH: 117
<212> TYPE: PRT
<213> ORGANISM: Artificial
<220> FEATURE:
<223> OTHER INFORMATION: Heavy chain variable region

<400> SEQUENCE: 38

```
Glu Val Asn Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Ser Ile Ser Gly Gly Gly Arg Tyr Thr Tyr Tyr Pro Asp Ser Met
    50                  55                  60

Lys Gly Arg Phe Thr Ile Ser Arg Asp Asn Ser Lys Asn Asn Leu Tyr
65                  70                  75                  80

Leu Gln Met Asn Ser Leu Arg Ala Glu Asp Thr Ala Val Tyr Tyr Cys
                85                  90                  95

Val Tyr Glu Tyr Phe Tyr Thr Met Asp Tyr Trp Gly Gln Gly Thr Leu
            100                 105                 110

Val Thr Val Ser Ser
        115
```

<210> SEQ ID NO 39
<211> LENGTH: 117
<212> TYPE: PRT
<213> ORGANISM: Artificial
<220> FEATURE:
<223> OTHER INFORMATION: Heavy chain variable region

<400> SEQUENCE: 39

```
Glu Val Asn Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Ser Ile Ser Gly Gly Gly Arg Tyr Thr Tyr Tyr Pro Asp Ser Met
    50                  55                  60

Lys Gly Arg Phe Thr Ile Ser Arg Asp Asn Ser Lys Asn Asn Leu Tyr
65                  70                  75                  80

Leu Gln Met Asn Ser Leu Arg Ala Glu Asp Thr Ala Val Tyr Tyr Cys
                85                  90                  95

Val Tyr Glu Tyr Phe Tyr Thr Met Asp Tyr Trp Gly Gln Gly Thr Leu
            100                 105                 110

Val Thr Val Ser Ser
        115
```

<210> SEQ ID NO 40
<211> LENGTH: 117
<212> TYPE: PRT
<213> ORGANISM: Artificial
<220> FEATURE:
<223> OTHER INFORMATION: Heavy chain variable region

<400> SEQUENCE: 40

Glu Val Asn Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Ser Ile Ser Gly Gly Gly Arg Tyr Thr Tyr Tyr Pro Asp Ser Met
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Tyr Glu Tyr Phe Tyr Thr Met Asp Tyr Trp Gly Gln Gly Thr Leu
            100                 105                 110

Val Thr Val Ser Ser
        115

<210> SEQ ID NO 41
<211> LENGTH: 117
<212> TYPE: PRT
<213> ORGANISM: Artificial
<220> FEATURE:
<223> OTHER INFORMATION: Heavy chain variable region

<400> SEQUENCE: 41

Glu Val Asn Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Thr Pro Gly Lys Gly Leu Glu Trp Val
        35                  40                  45

Ala Ser Ile Ser Gly Gly Gly Arg Tyr Thr Tyr Tyr Pro Asp Ser Met
    50                  55                  60

Lys Gly Arg Phe Thr Ile Ser Arg Asp Asn Ser Lys Asn Asn Leu Tyr
65                  70                  75                  80

Leu Gln Met Asn Ser Leu Arg Ala Glu Asp Thr Ala Val Tyr Tyr Cys
                85                  90                  95

Val Tyr Glu Tyr Phe Tyr Thr Met Asp Tyr Trp Gly Gln Gly Thr Leu
            100                 105                 110

Val Thr Val Ser Ser
        115

<210> SEQ ID NO 42
<211> LENGTH: 117
<212> TYPE: PRT
<213> ORGANISM: Artificial
<220> FEATURE:
<223> OTHER INFORMATION: Heavy chain variable region

<400> SEQUENCE: 42

Glu Val Asn Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Thr Pro Gly Lys Gly Leu Glu Trp Val
        35                  40                  45

```
Ala Ser Ile Ser Gly Gly Gly Arg Tyr Thr Tyr Tyr Pro Asp Ser Met
    50                  55                  60

Lys Gly Arg Phe Thr Ile Ser Arg Asp Asn Ser Lys Asn Asn Leu His
65                  70                  75                  80

Leu Gln Met Ser Ser Leu Arg Ala Glu Asp Thr Ala Val Tyr Tyr Cys
                85                  90                  95

Val Tyr Glu Tyr Phe Tyr Thr Met Asp Tyr Trp Gly Gln Gly Thr Leu
                100                 105                 110

Val Thr Val Ser Ser
        115

<210> SEQ ID NO 43
<211> LENGTH: 96
<212> TYPE: PRT
<213> ORGANISM: Artificial
<220> FEATURE:
<223> OTHER INFORMATION: IGKV3-11*01 (Germline database)

<400> SEQUENCE: 43

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

<210> SEQ ID NO 44
<211> LENGTH: 99
<212> TYPE: PRT
<213> ORGANISM: Artificial
<220> FEATURE:
<223> OTHER INFORMATION: IGHV3-23*04 (Germline database)
<220> FEATURE:
<221> NAME/KEY: MISC_FEATURE
<222> LOCATION: (99)..(99)
<223> OTHER INFORMATION: Xaa can be any naturally occurring amino acid

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Xaa

<210> SEQ ID NO 45
```

```
<211> LENGTH: 107
<212> TYPE: PRT
<213> ORGANISM: Artificial
<220> FEATURE:
<223> OTHER INFORMATION: Grafted humanized antibody light chain variable
      region

<400> SEQUENCE: 45

Glu Ile Val Leu Thr Gln Ser Pro Ala Thr Leu Ser Leu Ser Pro Gly
1               5                   10                  15

Glu Arg Ala Thr Leu Ser Cys Arg Ala Asn Gln Ser Ile Ser Asn Asn
            20                  25                  30

Leu His Trp Tyr Gln Gln Lys Pro Gly Gln Ala Pro Arg Leu Leu Ile
        35                  40                  45

Tyr Phe Ala Ser Gln Ser Ile Ser Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asp Asn Trp Pro Leu
                85                  90                  95

Thr Phe Gly Gly Gly Thr Lys Val Glu Ile Lys
            100                 105

<210> SEQ ID NO 46
<211> LENGTH: 117
<212> TYPE: PRT
<213> ORGANISM: Artificial
<220> FEATURE:
<223> OTHER INFORMATION: Grafted humanized antibody heavy chain variable
      region

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ser Ser Ile Ser Gly Gly Gly Arg Tyr Thr Tyr Tyr Pro Asp Ser Met
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Tyr Phe Tyr Thr Met Asp Tyr Trp Gly Gln Gly Thr Leu
            100                 105                 110

Val Thr Val Ser Ser
            115
```